US011720185B2

(12) United States Patent
Branquinho Gomes et al.

(10) Patent No.: US 11,720,185 B2
(45) Date of Patent: *Aug. 8, 2023

(54) METHOD AND SYSTEM FOR DETERMINING A CORRECT REPRODUCTION OF A MOVEMENT

(71) Applicant: SWORD HEALTH, S.A., Oporto (PT)

(72) Inventors: André Branquinho Gomes, Aveiro (PT); Ana Clara Ferreira Matos, Oporto (PT); Filipe Tavares Dos Santos, Oporto (PT); Luis Ungaro Pinto Coelho, Oporto (PT); Virgilio António Ferro Bento, Oporto (PT)

(73) Assignee: SWORD HEALTH, S.A., Oporto (PT)

( * ) Notice: Subject to any disclaimer, the term of this patent is extended or adjusted under 35 U.S.C. 154(b) by 0 days.

This patent is subject to a terminal disclaimer.

(21) Appl. No.: 17/747,865

(22) Filed: May 18, 2022

(65) Prior Publication Data

US 2023/0004236 A1    Jan. 5, 2023

Related U.S. Application Data

(63) Continuation of application No. 17/253,688, filed as application No. PCT/EP2019/066237 on Jun. 19, 2019, now Pat. No. 11,372,484.

(30) Foreign Application Priority Data

Jun. 20, 2018    (EP) ..................................... 18398006

(51) Int. Cl.
*G09G 5/00*    (2006.01)
*G06F 3/0346*    (2013.01)
(Continued)

(52) U.S. Cl.
CPC .......... *G06F 3/0346* (2013.01); *G06F 3/0383* (2013.01); *G06T 7/20* (2013.01); *G06F 1/163* (2013.01)

(58) Field of Classification Search
CPC ...... G06F 1/163; G06F 3/0346; G06F 3/0383; G06T 7/20; G16H 30/20
See application file for complete search history.

(56) References Cited

U.S. PATENT DOCUMENTS 6,831,603 B2    12/2004    Menache
7,395,181 B2    7/2008    Foxlin
(Continued)

FOREIGN PATENT DOCUMENTS

WO    WO-2012072961 A2    6/2012
WO    WO-2016079452 A1    5/2016
(Continued)

OTHER PUBLICATIONS

PCT/EP2019/066237 International Search Report and Written Opinion dated Sep. 17, 2019.

*Primary Examiner* — Insa Sadio
(74) *Attorney, Agent, or Firm* — Wilson Sonsini Goodrich & Rosati

(57) ABSTRACT

Method for determining a correct reproduction of a movement of a target based on a plurality of orientations thereof at different time instants at least including first and second time instants, the second time instant being posterior to the first time instant, the movement being defined by at least a first predetermined constraint, the first predetermined constraint being defined for first and second orientations of the plurality of orientations and defined by a start angle, an end angle and a first plane definition, comprising: providing a first plane and a second plane, each defined by the first plane definition, corresponding to the first and second time instants, respectively; providing a first pair of vectors by projecting the first orientation and the second orientation, corresponding to the first time instant, onto the first plane; providing a second pair of vectors by projecting the first orientation and the second orientation, corresponding to the second time instant, onto the second plane; computing first and second angles between the pair of vectors of the first and second pairs of vectors, respectively; and determining the correct reproduction of the movement if: the first angle is equal to or less than the start angle, and the second angle is equal to or greater than the end angle.

20 Claims, 8 Drawing Sheets

(51) Int. Cl.
 G06F 3/038 (2013.01)
 G06T 7/20 (2017.01)
 G06F 1/16 (2006.01)

(56) References Cited

U.S. PATENT DOCUMENTS

| | | |
|---|---|---|
| 7,811,333 B2 | 10/2010 | Jonsson et al. |
| 7,840,031 B2 | 11/2010 | Albertson et al. |
| 8,165,844 B2 | 4/2012 | Luinge et al. |
| 11,372,484 B2 | 6/2022 | Branquinho Gomes et al. |
| 2003/0054327 A1 | 3/2003 | Evensen |
| 2004/0077975 A1 | 4/2004 | Zimmerman |
| 2006/0247070 A1 | 11/2006 | Funk et al. |
| 2010/0144414 A1 | 6/2010 | Edis et al. |
| 2012/0183940 A1 | 7/2012 | Aragones et al. |
| 2014/0092009 A1* | 4/2014 | Yen ................ A63F 13/428 345/156 |
| 2015/0113417 A1* | 4/2015 | Yuen ................ H04L 67/306 715/736 |
| 2015/0335521 A1 | 11/2015 | Tedim Ramos Cruz et al. |
| 2016/0008661 A1 | 1/2016 | Ferro Bento et al. |

FOREIGN PATENT DOCUMENTS

| | | |
|---|---|---|
| WO | WO-2016146817 A1 | 9/2016 |
| WO | WO-2019243438 A1 | 12/2019 |

* cited by examiner

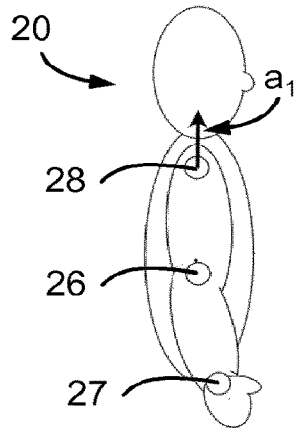 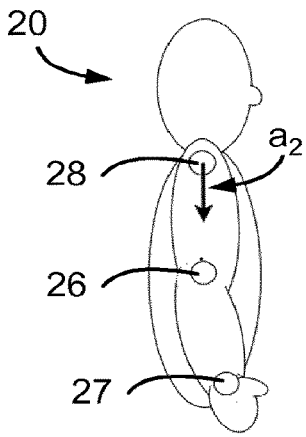
FIG. 8A          FIG. 8B
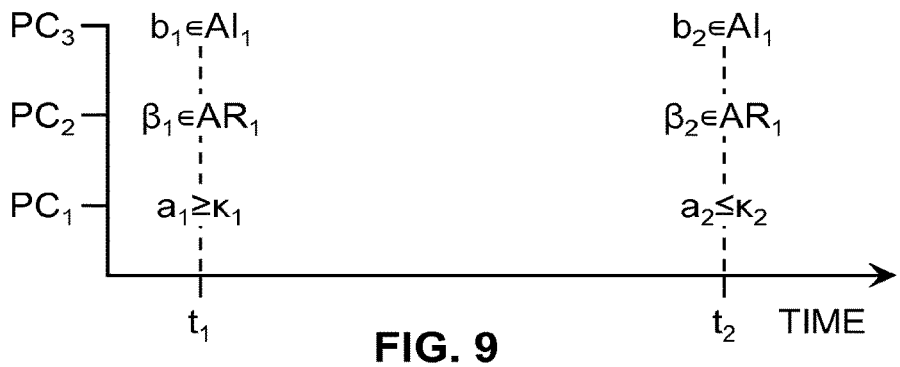
FIG. 9
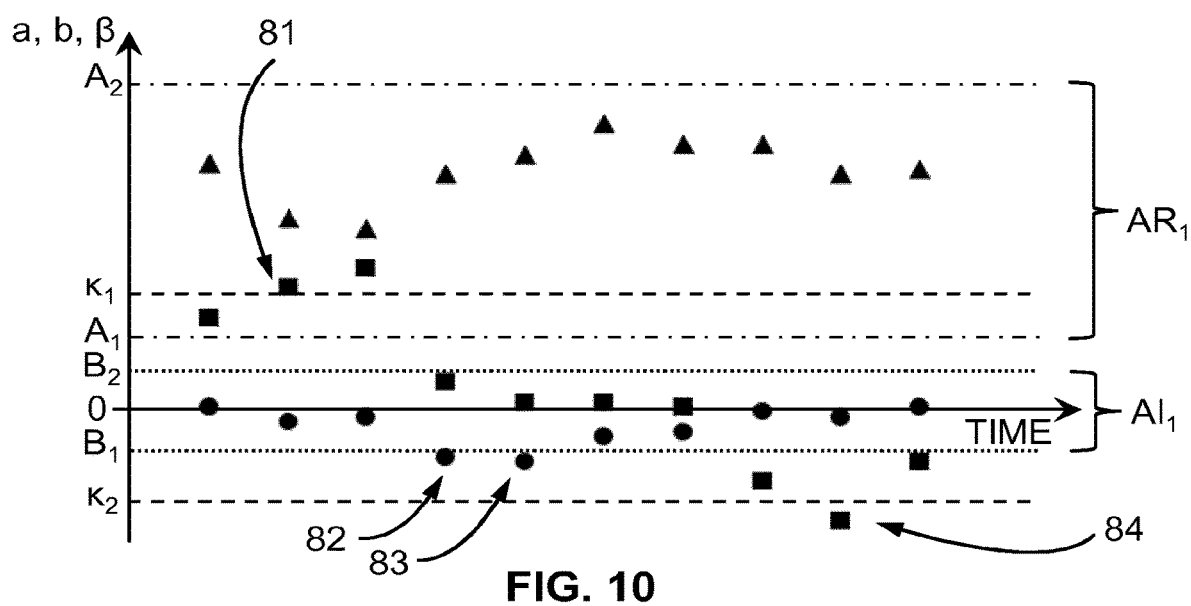
FIG. 10

METHOD AND SYSTEM FOR DETERMINING A CORRECT REPRODUCTION OF A MOVEMENT

CROSS-REFERENCE TO RELATED APPLICATIONS

This application is a continuation of U.S. application Ser. No. 17/253,688, filed on Dec. 18, 2020, which is a U.S. National Phase Application under 35 U.S.C. § 371 of International Application No. PCT/EP2019/066237, filed internationally on Jun. 19, 2019, which claims the benefit of priority to European Patent Application No. 18398006.9, filed on Jun. 20, 2018, all of which are hereby incorporated by reference in their entireties.

TECHNICAL FIELD

The present invention has its application within the sectors of motion tracking, and especially, in the industrial area engaged in providing tools for determining the correct realization or reproduction of a physical exercise.

STATE OF THE ART

Body-tracking technologies have focused a significant attention from the industrial and scientific communities, due to their potential applications, on diverse fields such as physical therapy, physical exercise monitoring, prosthetics, augmented reality and virtual reality, to name a few. Body-tracking enables to automatically determine a position of a user, either as a whole, or segmented by limbs, hence enabling automated position recognition and supervision.

For example, by determining the relative positions and orientations of a user's limbs and/or body segments (e.g. legs, arms, forearms, head, torso, etc), the correct realization or reproduction of a physical exercise entailing the carrying out of one or more movements can be automatically assessed. This enables the user, his/her fitness instructor or even his/her therapist to detect and possibly prevent harmful positions or movements that may result in injuries. Accurate, detailed and real-time posture and movement information is hence highly sought after in order to provide an efficient monitoring.

Body-tracking technologies can be roughly divided into two groups: those relying on wearable sensors attached to the user, and those relying on external information capture means, such as video cameras. For example, U.S. Pat. No. 8,165,844 B2 discloses a motion-tracking system providing 3D position and orientation information of a plurality of body segments. For this purpose the motion-tracking system comprises a plurality of wearable sensors that capture inertial information and, optionally, also magnetic field information. The information gathered from the plurality of wearable sensors is gathered at a Digital Signal Processor (DSP) or other form of programmable hardware, and processed through Kalman filters.

In another wearable sensor example, U.S. Pat. No. 7,811,333 B2 discloses a technique that captures time-resolved signals associated with the movements of a device attached to a limb. The captured signals are processed through autoregressive filters, and compared to stored data sets that characterize limb-motion events and/or phases. Time-resolved signals may be captured, for example, through accelerometers measuring displacements in three orthogonal planes. The captured information, and its comparison with the stored data sets, is preferably applied to control prosthetics or orthotic joints.

Regarding solutions based on external data capture, U.S. Pat. No. 6,831,603 B2 discloses a motion tracking technique where beacon signals are periodically transmitted from a reference tag and from object tags attached to the user or user's limbs being tracked. Beacon signals are received at an array of sensors installed in several positions of the zone under analysis. By measuring and comparing an identification code, a code phase and a carrier phase in each beacon signal, the relative position between the emitting tag and each sensor is determined for each sampling instant.

In another example, U.S. Pat. No. 7,395,181 B2 discloses a motion tracking system where a first estimate of the position and/or orientation of the user is performed through inertial measurements. This first estimate is then updated through an auxiliary technique, such as acoustic ranging, in order to enhance the system accuracy.

Finally, U.S. Pat. No. 7,840,031 B2 discloses an example of body-tracking technique based on three-dimensional (3D) images captured by one or more cameras aimed at the body of a user. A first 3D movement captured by the camera is used to predict a movement baseline, which is later compared to a second 3D movement in order to track changes in a range of body movement.

Regardless of the particular technique used for position and/or orientation acquisition, it is then necessary to process the acquired data in order to determine the user's posture and the movements the user makes. When this posture and movement determination are to be used for gaining knowledge of how the user moves and is positioned, a particularly challenging problem is recognizing a plethora of incorrect positions that may result in injury. In some cases, these incorrect positions are caused by subtle changes or small movements, hampering their detection. In other cases, the limbs causing the incorrect positions are not the ones performing the main movement (e.g. a faulty leg position in an arm exercise), thereby increasing the difficulty of properly detecting a possible harmful position and/or movement. Furthermore, it would be desirable that once the realization or reproduction of movement is determined to be within or outside of a predetermined range, that such information regarding the realization or reproduction of movement is provided so that the user, the fitness instructor or the therapist may know and take a measure if necessary.

Therefore, there is still the need in the state of the art of a technique for assessing how physical movements are carried out in a real-time manner, with a high accuracy and robustness. Furthermore, it is desirable that said technique is straightforwardly scalable to a numerous set of exercises and/or movements. Finally, in case a wrong movement or position is detected, it is desirable that the technique makes possible to provide information indicating the same.

DESCRIPTION OF THE INVENTION

A first aspect of the invention relates to a method for determining a correct reproduction of a movement of a target based on a plurality of orientations thereof at different time instants, the different time instants at least including first and second time instants, the second time instant being posterior to the first time instant, the movement being defined by at least a first predetermined constraint, the first predetermined constraint being defined for first and second orientations of the plurality of orientations and defined by a start angle, an end angle and a first plane definition, the method comprising: providing a first plane and a second plane, each defined by the first plane definition, corresponding to the first and second time instants, respectively; providing a first pair of vectors by projecting the first orientation and the second orientation, corresponding to the first time instant, onto the first plane; providing a second pair of vectors by projecting the first orientation and the second orientation, corresponding to the second time instant, onto the second plane; computing first and second angles between the pair of vectors of the first and second pairs of vectors, respectively; and determining the correct reproduction of the movement if: the first angle is equal to or less than the start angle, and the second angle is equal to or greater than the end angle.

The method makes possible to evaluate and, thus, determine whether a movement is correctly reproduced by processing the plurality of orientations that represent the movement that something or someone may be carrying out. The movement is considered to be reproduced correctly if each predetermined constraint defining the movement is fulfilled by the movement carried out by the target as determined by the plurality of orientations at the different time instants.

Each orientation represents how a segment or part of a target (e.g. an object, a person, etc.) is oriented. With pairs of orientations it may be established how the segments or parts are angularly moving one relative to the other. Each orientation of the plurality of orientations uses or is referenced to a same global reference frame (i.e. the orientations use a same coordinate system with same reference points). Preferably, each orientation of the plurality of orientations is a three-dimensional vector. Preferably, both vectors of each pair of vectors are three-dimensional vectors or two-dimensional vectors.

The first predetermined constraint and, possibly, additional or even each predetermined constraint has associated therewith a pair of orientations, a set of angles and a plane definition. The plane definition establishes what plane is provided, for each time instant, onto which the pairs of orientations are projected so as to determine whether the angular movement determined from the pair of orientations fulfills the condition(s) of the predetermined constraint. Accordingly, the set of angles of the first predetermined constraint comprises a start angle and an end angle that define the range of the movement, that is, from which angle (i.e. start angle) up to which angle (i.e. end angle) the movement is defined that the target has to carry out. The computed angles corresponding to different time instants are compared with said start and end angles in order to establish whether the movement has been correctly reproduced by the target.

In some embodiments, the movements are defined by more than one predetermined constraint. Each predetermined constraint limits more the movement against which the movement (of the target) resulting from the plurality of orientations and, optionally, one or more accelerations (at the different time instants) is to be compared. Hence, further computed angles or acceleration measurements (the latter provided by motion tracking means) are to be compared so as to determine whether the predetermined constraints are fulfilled and, thus, the movement is correctly reproduced. Mainly, the first predetermined constraint defines the motion range of the movement, whereas additional predetermined constraints (e.g. second, third, fourth predetermined constraints, etc.) define further limitations that shall be complied with by the target when carrying out the entire motion range of the movement.

In some embodiments, the movement is further defined by a second predetermined constraint, the second predetermined constraint being defined for third and fourth orientations of the plurality of orientations and defined by a first angular range and a second plane definition. In these embodiments, the method further comprises: providing a third plane, defined by the second plane definition, corresponding to the second time instant; providing a third pair of vectors by projecting the third orientation and fourth second orientation, corresponding to the second time instant, onto the third plane; and computing a third angle between the pair of vectors of the third pair of vectors. Further, determining the correct reproduction of the movement comprises that the third angle is within the first angular range. That is to say, that the third angle is equal to or greater than a lower threshold (i.e. lower angle) of the angular range and equal to or less than an upper threshold (i.e. upper angle) of the angular range.

The movement limitations resulting from the second predetermined constraint and/or additional predetermined constraints may relate to the movement of parts of the target different than those that should reproduce the movement as defined by the first predetermined constraint. Accordingly, said second and/or additional predetermined constraints are defined for orientations such that one or both of them are/is different from the first orientation and/or the second orientation.

In some embodiments, the movement is further defined by a second predetermined constraint, the second predetermined constraint being defined for the first and second orientations and defined by a first angular range and a second plane definition. In these embodiments, the method further comprises: providing a third plane, defined by the second plane definition, corresponding to the second time instant; providing a third pair of vectors by projecting the first orientation and the second orientation, corresponding to the second time instant, onto the third plane; and computing a third angle between the pair of vectors of the third pair of vectors. Further, determining the correct reproduction of the movement comprises that the third angle is within the first angular range.

The movement limitations resulting from the second predetermined constraint and/or additional predetermined constraints may relate to the movement of parts of the target that are the same as those that should reproduce the movement as defined by the first predetermined constraint. Accordingly, said second and/or additional predetermined constraints are/is defined for the first orientation and/or the second orientation.

In some embodiments, the method further comprises: providing a fourth plane, defined by the second plane definition, corresponding to the first time instant; providing a fourth pair of vectors by projecting each orientation for which the second predetermined constraint is defined (e.g. the first and second orientations, the third and fourth orientations, etc.), corresponding to the first time instant, onto the fourth plane; and computing a fourth angle between the pair of vectors of the fourth pair of vectors. In these embodiments, determining the correct reproduction of the movement further comprises that the fourth angle is within the first angular range.

Determining that a user has started to reproduce a movement may also depend on whether the second predetermined constraint and/or any additional predetermined constraints are/is fulfilled at the first time instant.

In some embodiments, the movement is further defined by additional predetermined constraints (e.g. third predetermined constraint, fourth predetermined constraint, etc.).

By way of example, the movement is further defined by a third predetermined constraint, the third predetermined constraint being defined for fifth and sixth orientations of the plurality of orientations and defined by a second angular range and a third plane definition. Further, the method comprises: providing a fourth plane, defined by the third plane definition, corresponding to the second time instant; providing a fourth pair of vectors by projecting the fifth orientation and the sixth orientation, corresponding to the second time instant, onto the fourth plane; and computing a fourth angle between the pair of vectors of the fourth pair of vectors. Further, determining the correct reproduction of the movement comprises that the fourth angle is within the second angular range. Additionally, the method may also comprise: providing a fifth plane, defined by the third plane definition, corresponding to the first time instant; providing a fifth pair of vectors by projecting the fifth orientation and the sixth orientation, corresponding to the first time instant, onto the fifth plane; computing a fifth angle between the pair of vectors of the fifth pair of vectors; and determining the correct reproduction of the movement comprises that the fifth angle is within the second angular range.

By way of another example, the movement is further defined by a third or fourth predetermined constraint, the third or fourth predetermined constraint being defined for third and fourth orientations of the plurality of orientations and defined by a second angular range and a third plane definition. Further, the method comprises: providing a fourth plane, defined by the third plane definition, corresponding to the second time instant; providing a fourth pair of vectors by projecting the third orientation and the fourth orientation, corresponding to the second time instant, onto the fourth plane; and computing a fourth angle between the pair of vectors of the fourth pair of vectors. Further, determining the correct reproduction of the movement comprises that the fourth angle is within the second angular range. Additionally, the method may also comprise: providing a fifth plane, defined by the third plane definition, corresponding to the first time instant; providing a fifth pair of vectors by projecting the third orientation and the fourth orientation, corresponding to the first time instant, onto the fifth plane; computing a fifth angle between the pair of vectors of the fifth pair of vectors; and determining the correct reproduction of the movement comprises that the fifth angle is within the second angular range.

In some embodiments, the different time instants further include a third time instant, the third time instant being posterior to the first time instant and anterior to the second time instant.

In some embodiments, the method further comprises: providing a fourth plane, defined by the first plane definition, corresponding to the third time instant; providing a fourth pair of vectors by projecting the first orientation and the second orientation, corresponding to the third time instant, onto the fourth plane; computing a fourth angle between the pair of vectors of the fourth pair of vectors; and determining the correct reproduction of the movement further comprises that the fourth angle is greater than the start angle and less than the end angle. In some of these embodiments, the method further comprises: providing a fifth plane, defined by the second plane definition, corresponding to the third time instant; providing a fifth pair of vectors by projecting each orientation for which the second predetermined constraint is defined (e.g. the first and second orientations, or the third and fourth orientations, etc.), corresponding to the third time instant, onto the fifth plane; computing a fifth angle between the pair of vectors of the fifth pair of vectors; and determining the correct reproduction of the movement further comprises that the fifth angle is within the first angular range.

When the plurality of orientations of the target is provided for more time instants, determining the correct reproduction of the movement involves comparing that the corresponding computed angles fall within the motion range of the movement as defined by the start and end angles, or that the computed angles fall within the corresponding angular ranges.

In some embodiments, the different time instants further include time instants posterior to the first time instant and anterior to the second time instant. For example, the different time instants further include a fourth time instant, the fourth time instant being posterior to the first time instant and anterior to the second time instant, and the fourth time instant being anterior or posterior to the third time instant.

In some embodiments, the method further comprises: providing a fifth plane, defined by the first plane definition, corresponding to the fourth time instant; providing a fifth pair of vectors by projecting the first orientation and the second orientation, corresponding to the fourth time instant, onto the fifth plane; and computing a fifth angle between the pair of vectors of the fifth pair of vectors; and determining the correct reproduction of the movement further comprises that the fifth angle is greater than the start angle and less than the end angle.

When the plurality of orientations of the target is provided for more time instants (e.g. fourth, fifth, sixth time instants, etc.), determining the correct reproduction of the movement involves comparing that the corresponding computed angles (of the second, third, fourth, etc. predetermined constraints) corresponding to said time instants fall within the corresponding angular ranges.

In some embodiments, the plane definition of each predetermined constraint (having a plane definition) of the movement comprises: an orientation of the plurality of orientations, said orientation defining a normal vector of the plane for each of the different time instants, and said orientation being different from the pair of orientations for which the predetermined constraint is defined; or a plane that is constant for the different time instants.

The plane definition may relate to an orientation of the plurality of orientations of the target. In this sense, determining whether the movement that the target carries out is reproduced correctly depends upon orientations of the target. Particularly, even though each predetermined constraint is defined for a pair of orientations that will be assessed in order to establish whether they fulfill the constraint (i.e. start and end angles, or angular range), an orientation of the target may influence said fulfillment. For example, when the target is a person and the pair of orientations of a predetermined constraint relate to the upper arm and the torso, respectively, the relative angular movement between the two may be based on a plane determined by the orientation of the upper arm or the torso.

As the target performs the movement, the orientation of the plane definition may change, thus the plane onto which the orientations corresponding to different time instants are projected may change as well.

The plane definition may also relate to a constant plane, for instance but without limitation, the horizontal or a vertical plane.

In some examples, the plane definition of one or more predetermined constraints is an orientation of the target and the plane definition of remaining predetermined constraints is a plane that is constant for the different time instants.

In some examples, one or more predetermined constraints are defined by a same plane definition.

In some embodiments, the method determines the correct reproduction of the movement of the target further based on one or more accelerations thereof at the different time instants, the movement being further defined by a second (and/or further) predetermined constraint, the second predetermined constraint being defined for a first acceleration of the one or more accelerations and defined by a first acceleration interval, and a first direction. In these embodiments, the method further comprises: providing an acceleration value corresponding to each time instant (e.g. first and second acceleration values corresponding to the first and second time instants, first to sixth acceleration values corresponding to first to sixth time instants, etc.), based on both the first acceleration and the first direction. Further, determining the correct reproduction of the movement comprises that at least one of the acceleration values is within the first acceleration interval. That is to say, that one, some or all of the acceleration values provided is/are equal to or greater than a lower threshold (i.e. lower acceleration threshold) of the acceleration interval and equal to or less than an upper threshold (i.e. upper acceleration threshold) of the acceleration interval.

The movement limitations resulting from the second predetermined constraint and/or additional predetermined constraints may relate to the acceleration of one or more parts of the tracked target. The acceleration values are computed based on the first direction, which establishes the movement limitation in terms of acceleration in that particular direction.

The first and second acceleration values are computed upon establishing the direction of the first acceleration measurements in accordance with the direction defined in the second (and/or further) predetermined constraint as the movement that is to be reproduced by the target inherently has a direction. In this sense, each acceleration value provided corresponds to the norm of the first acceleration at the particular time instant taking into account the direction (i.e. whether it goes in one direction or the opposite one) or, alternatively, corresponds to the component of the first acceleration along the first direction at the particular time instant. Therefore, if for example the target accelerates in one direction at the first time instant and stops at the second time instant, the first and second acceleration values will have opposite sign. The direction defined in the predetermined constraint may be, for example, an axis (e.g. a vertical axis, a horizontal axis, etc.), a three-dimensional vector, an angle, or a range of directions (in the form of axes, vectors or an angular range), any of which makes possible to establish in which direction the tracked target or part thereof is accelerating.

In some of these embodiments, the second (and/or further) predetermined constraint is further defined by a percentage threshold and a window size. In these embodiments, the method further comprises providing a sliding window with size equal to the window size, and sliding the sliding window from the first time instant to the second time instant such that the sliding window includes the provided acceleration values without exceeding the window size. Further, determining the correct reproduction of the movement comprises that each time the sliding window includes as many acceleration values as the window size, at least a percentage of the acceleration values within the window size equal to the percentage threshold is within the first acceleration interval. That is to say, every time the sliding window is full of acceleration values, a percentage resulting from a number of acceleration values in the window falling within the first acceleration interval divided by the window size is equal to or greater than the percentage threshold.

By applying the sliding window and the percentage threshold, the second (and/or further) predetermined constraint may limit in a greater or lesser degree the movement to be reproduced by the target since, in these cases, it may occur that at some time instants an acceleration value provided does not fall within the acceleration interval yet it is determined that the target correctly reproduced the movement. Said degree thus depends on both the window size and the percentage threshold.

In some embodiments, the method determines the correct reproduction of the movement of the target further based on one or more accelerations thereof at the different time instants, the movement being further defined by a third, fourth and/or further predetermined constraints, each such constraint being defined for a predetermined acceleration of the one or more accelerations (e.g. first, second, or further acceleration) and defined by a predetermined acceleration interval, and a predetermined direction. In these embodiments, the method further comprises, for each such predetermined constraint: providing an acceleration value corresponding to each time instant based on both the predetermined acceleration and the predetermined direction. Further, determining the correct reproduction of the movement comprises that at least one of the acceleration values is within the predetermined acceleration interval. Also, in some of these embodiments, each such constraint is further defined by a percentage threshold and a window size, and the correct reproduction of the movement follows the same procedure explained above.

In some embodiments, predetermined constraints aside from the first predetermined constraint are: predetermined constraints being defined for a pair of orientations of the plurality of orientations, predetermined constraints being defined for an acceleration, or a combination thereof.

Aside from the first predetermined constraint, the movement may thus be limited by predetermined constraints defining the angular movement between pairs of orientations, and/or predetermined constraints defining the linear movement of the tracked target or one or more parts thereof.

In some embodiments, the method further comprises, prior to the step of determining the correct reproduction of the movement, storing each predetermined constraint of the movement in a memory. In these embodiments, for each predetermined constraint one of the following is stored:

the two corresponding orientations for which the predetermined constraint is defined; the corresponding start and end angles, or the corresponding angular range; and the corresponding plane definition; and the corresponding acceleration for which the predetermined constraint is defined, the corresponding direction, the corresponding acceleration interval and, optionally, both the corresponding percentage threshold and the corresponding window size.

These data may be stored for one or more of the first, second, third, fourth, etc. predetermined constraints. The angular range preferably comprises a lower threshold and an upper threshold. The plane may be the mathematical definition of the plane or an indication of which orientation of the plurality of orientations is to be used for defining the plane (the normal vector thereof being the orientation). The direction preferably comprises a mathematical definition of an axis, a three-dimensional vector, an angle, or a range of directions in the form of axes, vectors or an angular range.

The acceleration interval preferably comprises a lower acceleration threshold and an upper acceleration threshold.

In some embodiments, determining the correct reproduction of the movement further comprises producing a feedback for each computed angle, the feedback comprising an indication of whether the computed angle fulfills each condition for determining that the movement is correctly reproduced. In some of these embodiments, determining the correct reproduction of the movement further comprises producing a feedback for each acceleration value provided, the feedback comprising an indication of whether the acceleration value provided fulfills each condition for determining that the movement is correctly reproduced.

The feedback indicates whether the computed angles corresponding to the first predetermined constraint fulfill that: the first angle is equal to or less than the start angle, the second angle is equal to or greater than the end angle, and any additional angle thereof (e.g. third angle) is greater than the start angle and less than the end angle. The feedback also indicates whether the computed angle(s) corresponding to the second and/or any additional predetermined constraint fulfill that the computed angle(s) is/are within the corresponding angular range(s).

When two or more predetermined constraints are analyzed, a hierarchical relation may be established between the same. If the computed angles corresponding to the first predetermined constraint do not fulfill each condition associated therewith, a negative feedback indicating an incorrect reproduction of the movement is produced. Otherwise, if the computed angle(s) or acceleration value(s) corresponding to the second predetermined constraint fulfills each condition associated therewith, a positive feedback indicating the correct reproduction of the movement is produced; whereas if the computed angle(s) or acceleration value(s) corresponding to the second predetermined constraint do not fulfill each condition associated therewith, a detailed feedback is produced, indicating that the second predetermined constraint is not verified.

That is, in case of a negative evaluation (i.e. the method detects that a movement is not performed correctly) the method preferably provides detailed feedback regarding which predetermined constraint or constraints are not fulfilled. If the movements of a user are to be evaluated with the method of the present disclosure, the user may be informed which predetermined constraints have not been fulfilled so that the user may try to adjust his or her movement so as to correctly reproduce it. The computational efficiency of the invention may make possible to provide this information in real-time.

Preferably, the method determines that the movement is not correctly reproduced if a computed angle, corresponding to a predetermined constraint and to at least one time instant that is posterior to the first time instant and anterior to the second time instant, does not fulfill each condition associated therewith. That is, if in said at least one time instant taking place between the first and the second time instants, a plane of a predetermined constraint is provided, the vectors corresponding to the projection of the pair of orientations onto the plane are provided, the angle between the vectors is computed, and the computed angle is outside the corresponding angular range (or is less than the start angle if it is the first predetermined task), the method determines that the movement is not correctly reproduced.

In some embodiments, the produced feedback may be at least one of: stored in an internal memory, transmitted through a communications network (wired or wireless), and displayed through a user interface.

In some embodiments, the target is a user. That is to say, the user is a person. In some other embodiments, the target is an object. For example but without limitation, the object may be a robot, an exoskeleton or exosuit.

In some embodiments, the method further comprises receiving, at the different time instants, each orientation of the plurality of orientations and, optionally, each acceleration of the one or more accelerations from motion tracking means. In some of these embodiments, receiving, at the different time instants, each orientation of the plurality of orientations and, optionally, each acceleration of the one or more accelerations from motion tracking means comprises: receiving, at the different time instants, the first orientation and, optionally, a first acceleration from a first sensor of the motion tracking means attached to a first segment of a user's body, and receiving, at the different time instants, the second orientation and, optionally, a second acceleration from a second sensor of the motion tracking means attached to a second segment of a user's body. In some of these embodiments, receiving, at the different time instants, each orientation of the plurality of orientations and, optionally, each acceleration of the one or more accelerations from motion tracking means comprises receiving, at the different time instants, additional orientations (e.g. third, fourth, fifth, sixth orientations, etc.) and, optionally, an acceleration from a respective additional sensor (e.g. third, fourth, fifth, sixth sensor, etc.) of the motion tracking means attached to a respective segment (e.g. third, fourth, fifth, sixth segment, etc.) of a user's body.

In some embodiments, the method further comprises sensing, at the different time instants, each orientation of the plurality of orientations and, optionally, each acceleration of the one or more accelerations with motion tracking means. In some of these embodiments, sensing, at the different time instants, each orientation of the plurality of orientations and, optionally, each acceleration of the one or more accelerations with motion tracking means comprises: sensing, at the different time instants, the first orientation and, optionally, a first acceleration with a first sensor of the motion tracking means attached to a first segment of a user's body, and sensing, at the different time instants, the second orientation and, optionally, a second acceleration with a second sensor of the motion tracking means attached to a second segment of a user's body. In some of these embodiments, sensing, at the different time instants, each orientation of the plurality of orientations and, optionally, each acceleration of the one or more accelerations with motion tracking means comprises sensing, at the different time instants, additional orientations (e.g. third, fourth, fifth, sixth orientations, etc.) and, optionally, an acceleration with a respective additional sensor (e.g. third, fourth, fifth, sixth sensor, etc.) of the motion tracking means attached to a respective segment (e.g. third, fourth, fifth, sixth segment, etc.) of a user's body.

In some embodiments, the first segment comprises a first limb of the user and the second segment comprises a second limb of the user. In some of these embodiments, the first limb and the second limb are attached to a same joint of the user. That is, the first limb is connected to the second limb by means of a joint. In some other embodiments, the first and second limbs are not attached to a same joint of the user.

A second aspect of the invention relates to a method for determining a correct reproduction of a movement of a target at least based on one or more accelerations thereof at different time instants, the different time instants at least including first and second time instants, the second time instant being posterior to the first time instant, the movement being defined by at least a first predetermined constraint, the first predetermined constraint being defined for a first acceleration of the one or more accelerations and defined by start and end acceleration thresholds, and a first direction, the method comprising: providing first and second acceleration values corresponding to the first and second time instants, respectively, based on both the first acceleration and the first direction; computing a first comparison between the first acceleration value and the start acceleration threshold; computing a second comparison between the second acceleration value and the end acceleration threshold; and determining the correct reproduction of the movement if: the first acceleration value is greater than or equal to the start acceleration threshold, and the second acceleration value is less than or equal to the end acceleration threshold.

The method makes possible to evaluate and, thus, determine whether a movement is correctly reproduced by processing first acceleration measurements corresponding to an acceleration that a target (e.g. an object, a person, a body member of a person) has been subjected to while a movement has been performed by said target. The movement is considered to be reproduced correctly if each predetermined constraint defining the movement is fulfilled by the movement performed by the target as determined from the first acceleration measurements at the different time instants.

The method is a computer-implemented method carried out by a device comprising a memory and a processor, such as a personal computer, a tablet, a digital signal processor, etc. The processor is configured to determine the correct reproduction of the movement by the target based on the measurements provided by motion tracking means that track the motion of the target. The motion tracking means are provided with one or more sensors that provide the acceleration of the target so that the movement performed by the target may be established based on said acceleration. In this sense, the motion tracking means may comprise e.g. a first sensor attachable to the target (for instance, to a first segment of a user's body) and adapted to measure the first acceleration.

The first and second acceleration values are computed upon establishing the direction of the first acceleration measurements in accordance with the direction defined in the predetermined constraint as the movement that is to be reproduced by the target inherently has a direction. In this sense, the first and second acceleration values correspond to the norm of the first acceleration at the first and second time instants taking into account the direction (i.e. whether it goes in one direction or the opposite one) or, alternatively, correspond to the component of the first acceleration along the first direction at the first and second time instants. Therefore, if for example the target accelerates in one direction at the first time instant and stops at the second time instant, the first and second acceleration values will have opposite sign. The direction defined in the predetermined constraint may be, for example, an axis (e.g. a vertical axis, a horizontal axis, etc.), a three-dimensional vector, an angle, or a range of directions (in the form of axes, vectors or an angular range), any of which makes possible to establish in which direction the tracked target or part thereof is accelerating.

By way of example, if the direction for which the movement is defined in the first predetermined constraint is a vertical direction, when the tracked target or part thereof accelerates in a direction that deviates from the defined direction it will be less likely that the first acceleration value is greater than or equal to the start acceleration threshold, and/or that the second acceleration value is less than or equal to the end acceleration threshold.

In some embodiments, the movements are defined by more than one predetermined constraint. Each predetermined constraint limits more the movement against which the movement (of the target) resulting from the one or more accelerations (e.g. the first acceleration) and, optionally, a plurality of orientations (at the different time instants) is to be compared. Hence, further acceleration measurements (provided by motion tracking means) or computed angles according to the first aspect of the invention are to be compared so as to determine whether the predetermined constraints are fulfilled and, thus, the movement is correctly reproduced.

In some embodiments, the movement is further defined by a second (and/or further) predetermined constraint, the second predetermined constraint being defined for a second acceleration of the one or more accelerations and defined by a first acceleration interval, and a second direction. In these embodiments, the method further comprises: providing an acceleration value corresponding to each time instant (e.g. third and fourth acceleration values corresponding to the first and second time instants), based on both the second acceleration and the second direction. Further, determining the correct reproduction of the movement comprises that at least one of the acceleration values is within the first acceleration interval. That is to say, that one, some or all of the acceleration values provided is/are equal to or greater than a lower threshold (i.e. lower acceleration threshold) of the acceleration interval and equal to or less than an upper threshold (i.e. upper acceleration threshold) of the acceleration interval.

The movement limitations resulting from the second predetermined constraint and/or additional predetermined constraints may further relate to the acceleration of one or more parts of the tracked target. The acceleration values are computed based on the direction defined in the particular predetermined constraint, said direction establishing the movement limitation in terms of acceleration in that particular direction.

The acceleration values are computed upon establishing the direction of the second acceleration measurements in accordance with the direction defined in the second (and/or further) predetermined constraint as the movement that is to be reproduced by the target inherently has a direction. Each acceleration value provided may correspond to the norm of the second acceleration at the particular time instant taking into account the defined direction (i.e. whether it goes in one direction or the opposite one) or, alternatively, correspond to the component of the second acceleration along the defined direction at the particular time instant.

In some of these embodiments, the second (and/or further) predetermined constraint is further defined by a percentage threshold and a window size. In these embodiments, the method further comprises providing a sliding window with size equal to the window size, and sliding the sliding window from the first time instant to the second time instant such that the sliding window includes the provided acceleration values without exceeding the window size. Further, determining the correct reproduction of the movement comprises that each time the sliding window includes as many acceleration values as the window size, at least a percentage of the acceleration values within the window size equal to the percentage threshold is within the first acceleration interval. That is to say, every time the sliding window is full of acceleration values, a percentage resulting from a number of acceleration values in the window falling within the first acceleration interval divided by the window size is equal to or greater than the percentage threshold.

By applying a sliding window and a percentage threshold, the second (and/or further) predetermined constraint may limit in a greater or lesser degree the movement to be reproduced by the target.

In some embodiments, the different time instants further include a third time instant, the third time instant being posterior to the first time instant and anterior to the second time instant.

In some embodiments, the different time instants further include time instants posterior to the first time instant and anterior to the second time instant. For example, the different time instants further include a fourth time instant, the fourth time instant being posterior to the first time instant and anterior to the second time instant, and the fourth time instant being anterior or posterior to the third time instant.

In some embodiments, the movement is further defined by a third, fourth and/or further predetermined constraints, each such constraint being defined for a predetermined acceleration of the one or more accelerations (e.g. second, third, or further acceleration) and defined by a predetermined acceleration interval, and a predetermined direction. In these embodiments, the method further comprises, for each such predetermined constraint: providing an acceleration value corresponding to each time instant based on both the predetermined acceleration and the predetermined direction. Further, determining the correct reproduction of the movement comprises that at least one of the acceleration values is within the predetermined acceleration interval. Also, in some of these embodiments, each such constraint is further defined by a percentage threshold and a window size, and the correct reproduction of the movement follows the same procedure explained above.

In some embodiments, the method determines the correct reproduction of the movement of the target further based on a plurality of orientations thereof at the different time instants, the movement being further defined by a second (and/or further) predetermined constraint, the second predetermined constraint being defined for two orientations of the plurality of orientations (e.g. first and second orientations) and defined by a start angle, an end angle and a plane definition. In these embodiments, the method further comprises: providing as many planes as time instants are, each plane being defined by the plane definition and corresponding to one time instant (e.g. first and second planes corresponding to the first and second time instants, first to sixth planes corresponding to first to sixth time instants, etc.); for each time instant, providing as many pairs of vectors as planes are by projecting the first orientation and the second orientation, corresponding to the time instant, onto a respective plane (e.g. for first and second time instants, first and second pairs of vectors are provided by projecting the two orientations onto the first and second planes corresponding to the first and second time instants); and for each pair of vectors, computing an angle between the pair of vectors. Further, determining the correct reproduction of the movement comprises that a first angle (corresponding to the first time instant) is equal to or less than the start angle, a second angle (corresponding to the second time instant) is equal to or greater than the end angle, and, optionally, any computed angle corresponding to a time instant between the first and the second time instants (e.g. a third angle corresponding to a third time instant, the third time instant being posterior to the first time instant and anterior to the second time instant) is equal to or greater than the start angle and equal to or less than the end angle.

The first predetermined constraint limits the movement in terms of a linear displacement, whereas further predetermined constraint(s) limit the movement in terms of an angular movement between a pair of orientations of the tracked target.

In some embodiments, predetermined constraints aside from the first predetermined constraint are: predetermined constraints being defined for an acceleration, predetermined constraints being defined for a pair of orientations of the plurality of orientations, or a combination thereof.

In some embodiments, determining the correct reproduction of the movement comprises producing a feedback for each acceleration value provided, the feedback comprising an indication of whether the acceleration value provided fulfills each condition for determining that the movement is correctly reproduced. In some of these embodiments, determining the correct reproduction of the movement further comprises producing a feedback for each computed angle, the feedback comprising an indication of whether the computed angle fulfills each condition for determining that the movement is correctly reproduced.

In some embodiments, the produced feedback may be at least one of: stored in an internal memory, transmitted through a communications network (wired or wireless), and displayed through a user interface.

In some embodiments, the target is a user. That is to say, the user is a person. In some other embodiments, the target is an object. For example but without limitation, the object may be a robot, an exoskeleton or exosuit.

In some embodiments, the method further comprises receiving, at the different time instants, each acceleration of the one or more accelerations and, optionally, each orientation of the plurality of orientations from motion tracking means. In some of these embodiments, receiving, at the different time instants, each acceleration of the one or more accelerations and, optionally, each orientation of the plurality of orientations from motion tracking means comprises: receiving, at the different time instants, the first acceleration and, optionally, a first orientation from a first sensor of the motion tracking means attached to a first segment of a user's body. In some of these embodiments, receiving, at the different time instants, each acceleration of the one or more accelerations and, optionally, each orientation of the plurality of orientations from motion tracking means further comprises: receiving, at the different time instants, a second acceleration and/or a second orientation from a second sensor of the motion tracking means attached to a second segment of a user's body. In some of these embodiments, receiving, at the different time instants, each acceleration of the one or more accelerations and, optionally, each orientation of the plurality of orientations from motion tracking means comprises receiving, at the different time instants, additional accelerations (e.g. third, fourth, fifth, sixth accelerations, etc.) and/or an additional orientation of the plurality of orientations (e.g. third, fourth, fifth, sixth orientations, etc.) from a respective additional sensor (e.g. third, fourth, fifth, sixth sensor, etc.) of the motion tracking means attached to a respective segment (e.g. third, fourth, fifth, sixth segment, etc.) of a user's body.

In some embodiments, the method further comprises sensing, at the different time instants, each acceleration of the one or more accelerations and, optionally, each orientation of the plurality of orientations with motion tracking means. In some of these embodiments, sensing, at the different time instants, each acceleration of the one or more accelerations and, optionally, each orientation of the plurality of orientations with motion tracking means comprises: sensing, at the different time instants, the first acceleration and, optionally, a first orientation with a first sensor of the motion tracking means attached to a first segment of a user's body. In some of these embodiments, sensing, at the different time instants, each acceleration of the one or more accelerations and, optionally, each orientation of the plurality of orientations with motion tracking means further comprises: sensing, at the different time instants, the second acceleration and/or a second orientation with a second sensor of the motion tracking means attached to a second segment of a user's body. In some of these embodiments, sensing, at the different time instants, each acceleration of the one or more accelerations and, optionally, each orientation of the plurality of orientations with motion tracking means comprises sensing, at the different time instants, additional accelerations (e.g. third, fourth, fifth, sixth accelerations, etc.) and/or an additional orientation of the plurality of orientations (e.g. third, fourth, fifth, sixth orientations, etc.) with a respective additional sensor (e.g. third, fourth, fifth, sixth sensor, etc.) of the motion tracking means attached to a respective segment (e.g. third, fourth, fifth, sixth segment, etc.) of a user's body.

In some embodiments, the method further comprises, prior to the step of determining the correct reproduction of the movement, storing each predetermined constraint of the movement in a memory. In these embodiments, for each predetermined constraint one of the following is stored:

the corresponding acceleration for which the predetermined constraint is defined, the corresponding start and end acceleration thresholds, and the corresponding direction;

the corresponding acceleration for which the predetermined constraint is defined, the corresponding direction, the corresponding acceleration interval and, optionally, both the corresponding percentage threshold and the corresponding window size; and the two corresponding orientations for which the predetermined constraint is defined, the corresponding angular range; and the corresponding plane definition.

In some embodiments, the plane definition of each predetermined constraint (having a plane definition) of the movement comprises: an orientation of the plurality of orientations, said orientation defining a normal vector of the plane for each of the different time instants, and said orientation being different from the pair of orientations for which the predetermined constraint is defined; or a plane that is constant for the different time instants.

In some embodiments, the first segment comprises a first limb of the user and the second segment comprises a second limb of the user. In some of these embodiments, the first limb and the second limb are attached to a same joint of the user. That is, the first limb is connected to the second limb by means of a joint. In some other embodiments, the first and second limbs are not attached to a same joint of the user.

Further, same or similar combination of predetermined constraints as described with reference to the first aspect of the invention may also form part of particular embodiments of this aspect as it will be readily apparent to the skilled person, the same being also disclosed within the scope of the present disclosure.

A third aspect of the present invention relates to a device for determining a correct reproduction of a movement of a target. The device comprises a processor configured or programmed to perform the steps of a method according to the first aspect of the invention, or the steps of a method according to the second aspect of the invention.

The device may comprise:

A memory that provides the reference to the pair of orientations and/or acceleration(s) associated with some or each predetermined constraint, the plane definition and/or direction associated with some or each predetermined constraint, and the set of angles (start and end angles, or angular range) or accelerations (start and end acceleration thresholds, or acceleration interval) associated with some or each predetermined constraint; optionally, it may also provide the reference to both the predetermined percentage and the window size associated with some or each predetermined constraint.

A user interface that may display the produced feedback so that a user may know the outcome of the determination and, in some cases, why the movement is not reproduced correctly. The user interface may comprise any number of input and/or output means known in the state of the art, such as buttons, screens, touch-screens, speakers, etc. The device may also be implemented without any interface accessible to the user; the evaluation results may be stored in a memory for ulterior analysis, or transmitted to a remote server or application.

First communication means, adapted to receive data from motion tracking means. Said first communication means may be implemented according to a wired or wireless technology and protocol known by the skilled person, for instance but without limitation, Bluetooth communications, cellular network communications (e.g. GSM, UMTS, LTE), wireless LAN communications, etc. Therefore, the first communication means may comprise an antenna, a connection port to a router, etc. adapted to receive a plurality of orientations and/or accelerations from the motion tracking means, either directly (i.e. from the motion tracking means) or through a communications network.

Second communication means, which connect the device with a remote server or application for transmission of data thereto. Said second communication means may be implemented according to a wired or wireless technology and protocol known by the skilled person, for instance but without limitation, Bluetooth communications, cellular network communications (e.g. GSM, UMTS, LTE), wireless LAN communications, etc.

A fourth aspect of the present invention relates to a system for determining a correct reproduction of a movement of a target. The system comprises: a device according to the third aspect of the invention; and a motion tracking means for sensing the plurality of orientations and/or the one or more accelerations.

In some embodiments, the motion tracking system at least comprises a first sensor adapted to measure the first orientation and a second sensor adapted to measure the second orientation. In some of these embodiments, the first sensor is further adapted to measure the first acceleration. In some of these embodiments, the second sensor is further adapted to measure the second acceleration. In some of these embodiments, the motion tracking system further comprises additional sensors adapted to measure additional orientations and/or accelerations (e.g. third, fourth, fifth, sixth sensors adapted to measure third, fourth, fifth, sixth orientations and/or accelerations, respectively).

In some embodiments, the motion tracking system at least comprises a first sensor adapted to measure the first acceleration. In some of these embodiments, the motion tracking system further comprises a second sensor adapted to measure the second acceleration. In some of these embodiments, the first sensor is further adapted to measure the first orientation and the second sensor is further adapted to measure the second orientation. In some of these embodiments, the motion tracking system further comprises additional sensors adapted to measure additional accelerations and/or orientations (e.g. third, fourth, fifth, sixth sensors adapted to measure third, fourth, fifth, sixth accelerations and/or orientations, respectively).

In some embodiments, the first sensor is attachable to a first segment of a user's body. In some of these embodiments, the second sensor is attachable to a second segment of a user's body. In some of these embodiments, each additional sensor (e.g. third, fourth, fifth, sixth sensor) is attachable to another segment (e.g. third, fourth, fifth, sixth segment) of a user's body.

In some embodiments, the system further comprises communications means for communicatively coupling the device with the motion tracking means.

In a fifth aspect of the present invention, a computer program product is disclosed, comprising instructions which, when the program is executed by a device, cause the device to carry out the method of the first aspect of the invention, or the method of the second aspect of the invention. The device may be a computer, a digital signal processor, a field-programmable gate array, an application-specific integrated circuit, a micro-processor, a microcontroller, or any other form of programmable hardware.

In a sixth aspect of the present invention, a computer-readable storage medium is disclosed, comprising instructions which, when the program is executed by a computer, cause the computer to carry out the method of the first aspect of the invention, or the method of the second aspect of the invention.

A seventh aspect of the present invention relates to a method for supervising a physical exercise of a user, the physical exercise comprising a movement, the method comprising: detecting the movement of the user with motion tracking means; providing a plurality of orientations and/or one or more accelerations resulting from the detection of the movement; and one of:

determining, with a method according to the first aspect of the invention, correct reproduction of the movement of the user based on the plurality of orientations provided and, optionally, also based on the one or more accelerations; and determining, with a method according to the second aspect of the invention, correct reproduction of the movement of the user based on the one or more accelerations and, optionally, also based on the plurality of orientations provided.

The method makes possible to supervise the physical exercises performed by a target, in this case the user. The detected movements are provided in the form of orientations and/or accelerations and, subsequently, the movements performed by the user are assessed in order to determine whether the reproduction thereof is correct. Upon determining whether the reproduction of the movement is correct, the same user or a different user may be informed of the determination. Accordingly, the user may gain knowledge of how he/she is performing the move so as to continue performing it in that way or correct it if necessary.

In some embodiments, the physical exercise is a fitness exercise, and the movement is a fitness movement.

In some embodiments, the physical exercise is a rehabilitation exercise, and the movement is a rehabilitation movement.

Similar advantages as those described for the first aspect of the invention or the second aspect of the invention may also be applicable to the third, fourth, fifth, sixth and seventh aspects of the invention.

Additional advantages and features of the invention will become apparent from the detailed description that follows and will be particularly pointed out in the appended claims.

BRIEF DESCRIPTION OF THE DRAWINGS

To complete the description and in order to provide for a better understanding of the invention, a set of drawings is provided. Said drawings form an integral part of the description and illustrates embodiments of the invention, which should not be interpreted as restricting the scope of the invention, but just as examples of how the invention can be carried out. The drawings comprise the following figures:

FIGS. 8A-8B schematically illustrate a movement performed by a user.

FIGS. 9-11 illustrate determination of correct reproduction of a movement with methods according to embodiments of the invention.

DESCRIPTION OF WAYS OF CARRYING OUT THE INVENTION

Figure 1A:
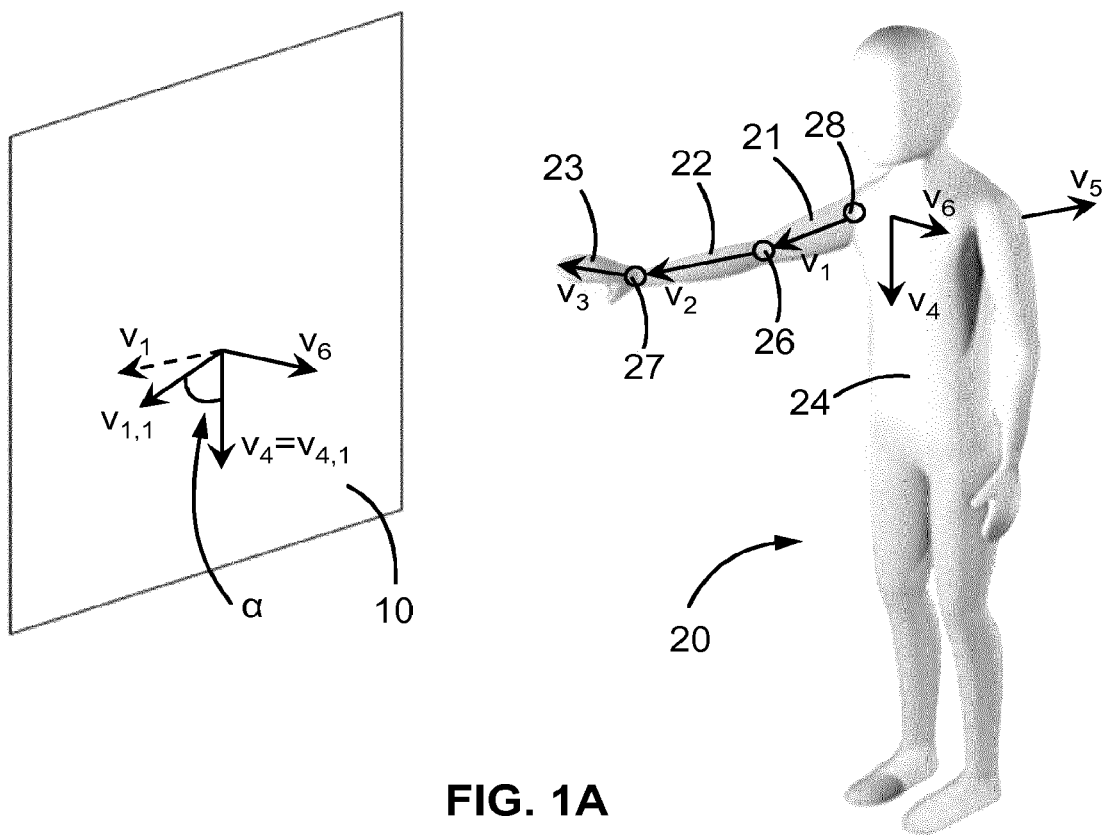
FIGS. 1A-1B show examples of orientations of a user.
Figure 1B:
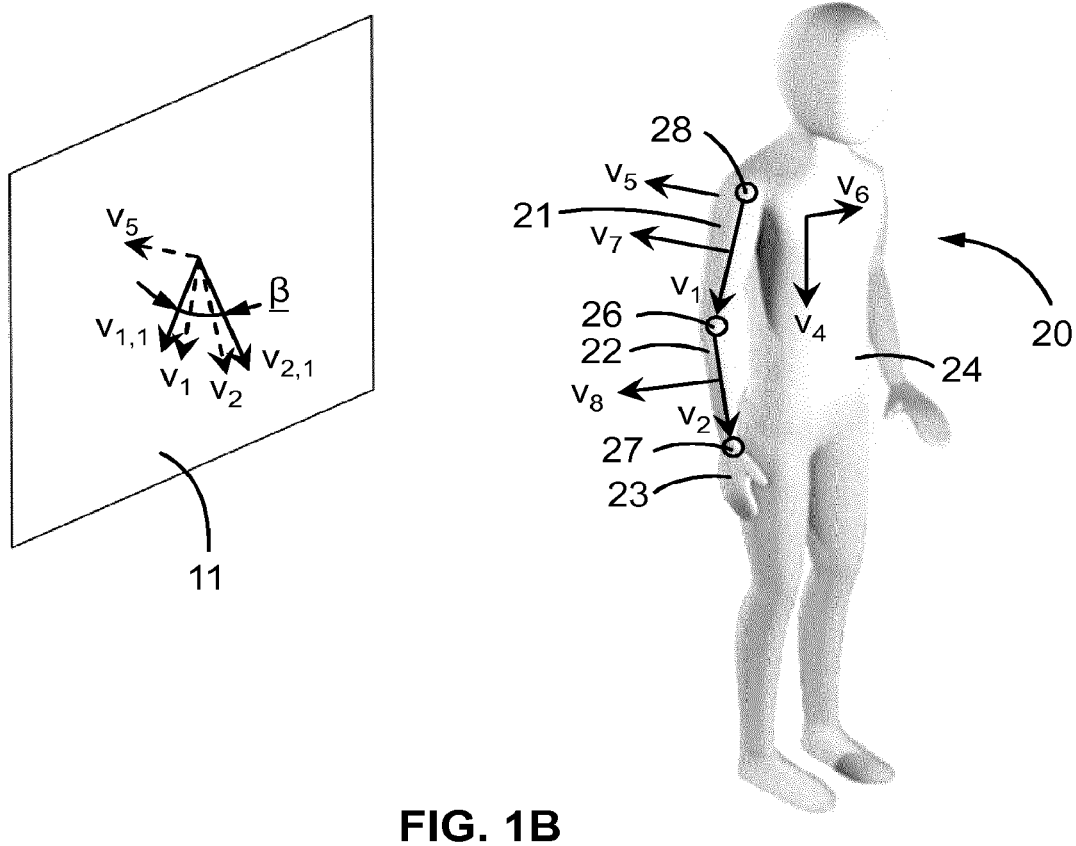

FIGS. 1A-1B schematically exemplify scenarios of application of particular embodiments of the method, device and system of the invention, where the correct reproduction of a movement is determined based on orientation measurements of multiple segments (21-24) of a user's body (20). The user (20) has a plurality of limbs (21-24), some of which are connected to other limbs (21-24) through a common joint (26-28).

Each limb (21-24) defines one or more orientations ($v_1$-$v_8$), for instance but not limited to, as three-dimensional vectors. For example, in FIGS. 1A-1B, three different orientations ($v_4$-$v_6$) of a torso (24) are illustrated; in this case, two orientations ($v_4$, $v_6$) define the two axes of the torso (24) and, thus, are contained in a plane of the torso (24), and a third orientation ($v_5$) defines the normal vector of the plane of the torso (24). Similarly, each of the right upper and lower arms (21, 22) is illustrated defining two different orientations: one orientation along the segment of the limb and one orientation as a normal vector of a plane containing the segment.

When carrying out the method of the present disclosure, which in several embodiments is a computer-implemented method, in some embodiments each orientation ($v_1$-$v_8$) may be projected onto a plane (10) in accordance with a plane definition of a predetermined constraint. By way of example, the plane (10) of FIG. 1A is defined by orientation $v_6$ of the user, particularly, the normal vector of the plane (10) is the orientation $v_6$ of the width dimension of the torso (24). As illustrated in FIG. 1A, when orientations $v_1$ and $v_4$ are projected onto the plane (10), the angle between the resulting vectors may be computed, such as the angle alpha between the vectors $v_{1,1}$ and $v_{4,1}$. By way of another example, the plane (11) of FIG. 1B is defined by orientation $v_5$ of the user, particularly, the normal vector of the plane (11) is the orientation $v_5$ of the normal vector of the plane of the torso (24). As illustrated in FIG. 1B, when orientations $v_1$ and $v_2$ are projected onto the plane (11), the angle between the resulting vectors may be computed, such as the angle beta between the vectors $v_{1,1}$ and $v_{2,1}$.

FIGS. 2A-2D schematically illustrate a movement performed by the user (20).

Figure 2A:
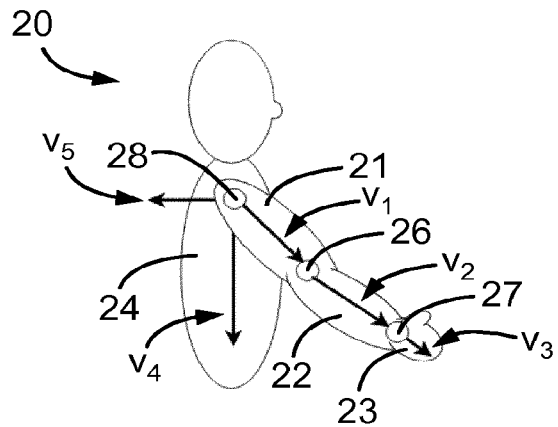
FIGS. 2A-2D schematically illustrate a movement performed by a user.
Figure 2B:
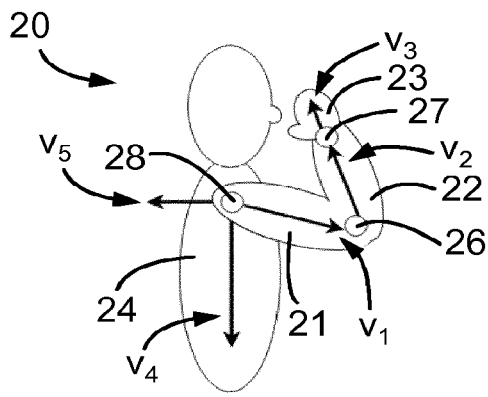
Figure 2C:
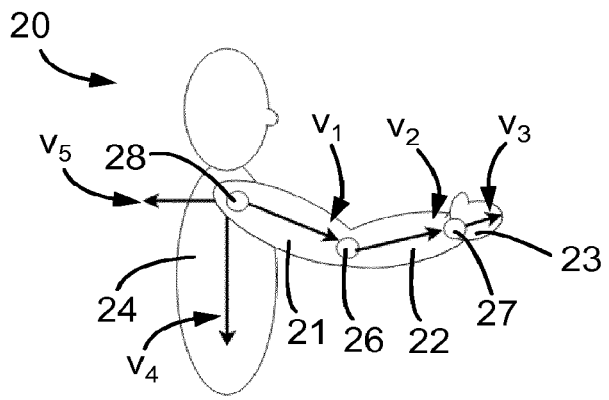
Figure 2D:
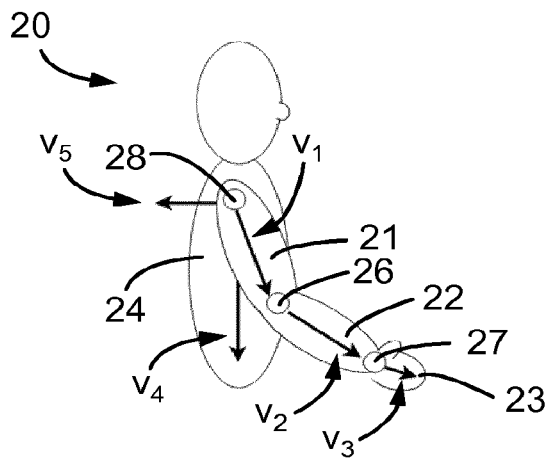

FIG. 2A shows the user (20) about to start an elbow flexion movement at a first time instant (e.g. $t_1$). The user (20) is standing upright with the right arm (21-23) extended such that an angle is formed with respect to the orientation $v_4$ of the torso (24). FIG. 2B shows the user (20) once he/she has finished the elbow flexion movement at a second time instant (e.g. $t_2$) that is posterior to the first time instant, that is, $t_2 > t_1$. The user (20) is standing upright with the right arm (21-23) bent, and such that the upper arm (21) forms an angle with respect to the orientation $v_4$ of the torso (24) that is similar to the angle of FIG. 2A. FIGS. 2C and 2D show the user (20), at time instants (for example third and fourth time instants, e.g. $t_3$ and $t_4$) occurring between the first and the second time instants (that is, $t_1 < t_3 < t_2$ and $t_1 < t_4 < t_2$), partially bending the right arm (21-23) so as to perform the elbow flexion movement.

FIGS. 3A-3D partially illustrate, in relation to the movement of FIGS. 2A-2D, methods according to embodiments of the invention in which a movement is at least defined by a first predetermined constraint.

Figure 3A:
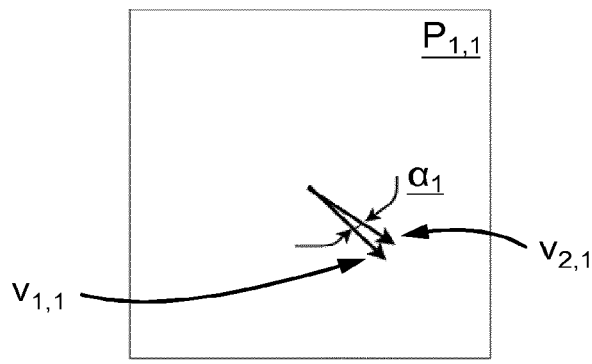
FIGS. 3A-3D, 4A-4D partially illustrate methods according to embodiments of the invention in relation to the movement of FIGS. 2A-2D.
Figure 3B:
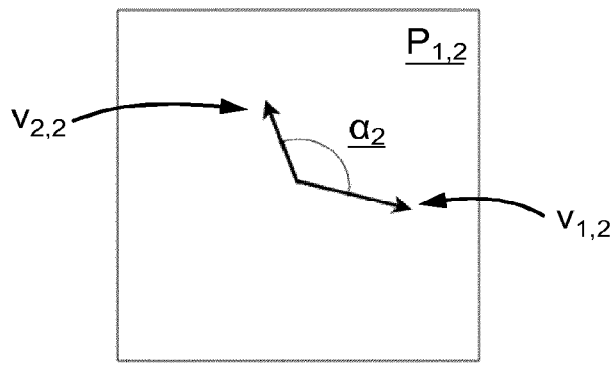
Figure 3C:
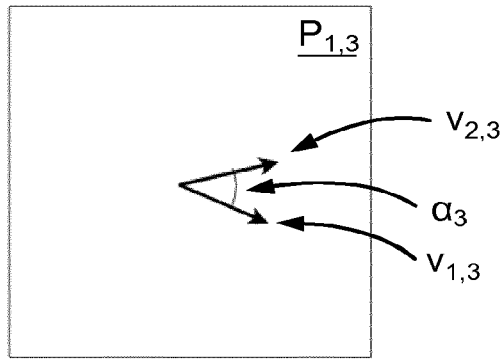
Figure 3D:
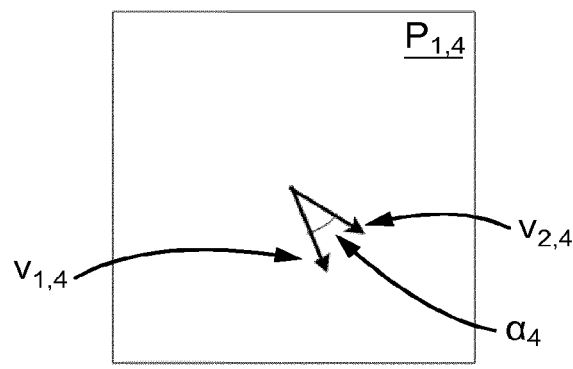

FIG. 3A shows a plane $P_{1,1}$ provided for the first time instant of FIG. 2A. The plane $P_{1,1}$ corresponds to the first predetermined constraint and is defined by a plane definition (of the first predetermined constraint) based on the orientation $v_6$ (as normal vector of the plane) of the user (20) at the first time instant. Projected onto said plane are orientations $v_1$ and $v_2$ of the user (20) at the first time instant, thereby providing vectors $v_{1,1}$ and $v_{2,1}$, respectively. The angle $\alpha_1$ between the two vectors may then be computed and compared with the start and end angles of the first predetermined constraint. FIG. 3B shows a plane $P_{1,2}$ provided for the second time instant of FIG. 2B based on the orientation $v_6$ at the second time instant. The orientations $v_1$ and $v_2$ of the user (20) at the second time instant are projected onto the plane $P_{1,2}$ thereby providing vectors $v_{1,2}$ and $v_{2,2}$, respectively, so that the angle $\alpha_2$ between the two vectors may be computed and compared with the start and end angles of the first predetermined constraint. FIGS. 3C and 3D show planes $P_{1,3}$ and $P_{1,4}$ provided for third and fourth time instants (as in FIGS. 2C and 2D), both taking place between the first and the second time instants, and based on the orientation $v_6$ at those time instants. The orientations $v_1$ and $v_2$ of the user (20) at those time instants are projected onto the plane $P_{1,3}$, thereby providing vectors $v_{1,3}$ and $v_{2,3}$, respectively, and onto the plane $P_{1,4}$, thereby providing vectors $v_{1,4}$ and $v_{2,4}$, respectively. The angles $\alpha_3$ and $\alpha_4$ between each pair of vectors may be computed and compared with the start and end angles of the first predetermined constraint.

In one exemplary method explained with reference to FIGS. 3A-3D, the movement to be reproduced by the user (20) is defined by a first predetermined constraint for the orientations $v_1$ and $v_2$ of the user (20); the first predetermined constraint is defined by a start angle (e.g. $SA_1$, for example 10°), an end angle (e.g. $EA_1$, for example 90°) and a plane definition (e.g. $P_1$) with which planes $P_{1,1}$ to $P_{1,4}$ are provided. The angle $\alpha_1$ (corresponding to $t_1$) is less than or equal to $SA_1$, therefore the user (20) has not started the reproduction of the movement yet. The angle $\alpha_2$ (corresponding to $t_2$) is greater than or equal to $EA_1$, therefore the user (20) has finished the reproduction of the movement.

If only the orientations corresponding to time instants $t_1$ and $t_2$ were provided by motion tracking means, the method would determine that the user (20) correctly reproduced the movement. If the motion tracking means also provided the orientations of the user (20) corresponding to time instant $t_3$, since the angle $\alpha_3$ is greater than $SA_1$ and less than $EA_1$, the method would also determine that the user (20) correctly reproduced the movement. Further, if the motion tracking means also provided the orientations of the user (20) corresponding to time instant $t_4$, since the angle $\alpha_4$ is greater than $SA_1$ and less than $EA_1$, the method would also determine that the user (20) correctly reproduced the movement.

Figure 4A:
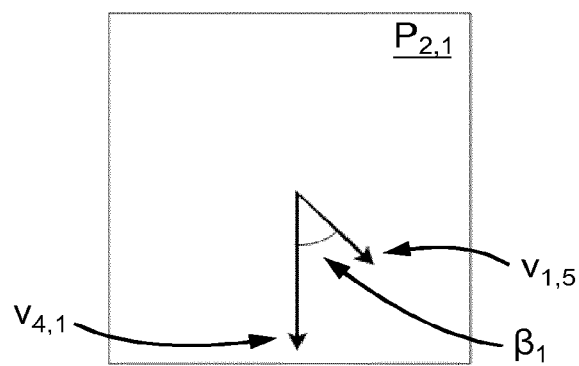
Figure 4B:
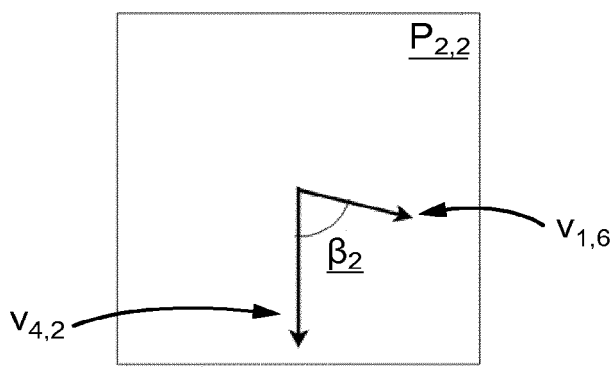

FIGS. 4A-4B partially illustrate, in relation to the movement of FIGS. 2A-2D, methods according to embodiments of the invention in which a movement is at least defined by first and second predetermined constraints.

Figure 4C:
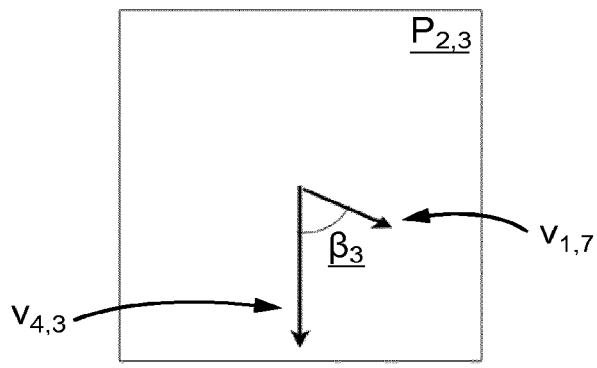
Figure 4D:
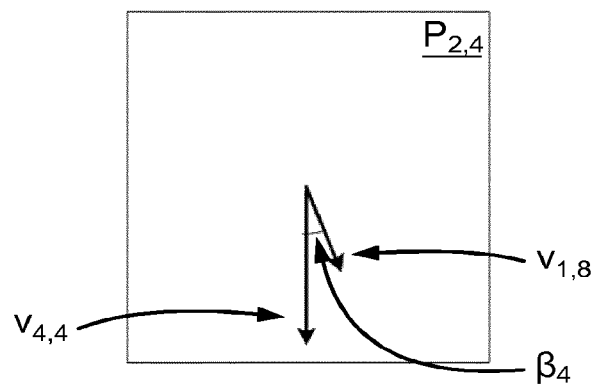

FIG. 4A shows a plane $P_{2,1}$ provided for the first time instant of FIG. 2A. The plane $P_{2,1}$ corresponds to a second predetermined constraint and is defined by a plane definition (of the second predetermined constraint, e.g. $P_2$) based on the orientation $v_7$, that is a normal vector of the right upper arm (21). Projected onto said plane are orientations $v_1$ and $v_4$ of the user (20) at the first time instant, thereby providing vectors $v_{1,5}$ and $v_{4,1}$, respectively. The angle $\beta_1$ between the two vectors may then be computed and compared with the angular range of the second predetermined constraint. FIG. 4B shows a plane $P_{2,2}$ provided for the second time instant of FIG. 2B based on the orientation $v_7$ at the second time instant. The orientations $v_1$ and $v_4$ of the user (20) at the second time instant are projected onto the plane $P_{2,2}$ thereby providing vectors $v_{1,6}$ and $v_{4,2}$, respectively, so that the angle $\beta_2$ between the two vectors may be computed and compared with the angular range. FIGS. 4C and 4D show planes $P_{2,3}$ and $P_{2,4}$ provided for third and fourth time instants (as in FIGS. 2C and 2D), both taking place between the first and the second time instants, and based on the orientation $v_7$ at those time instants. The orientations $v_1$ and $v_4$ of the user (20) at those time instants are projected onto the plane $P_{2,3}$, thereby providing vectors $v_{1,7}$ and $v_{4,3}$, respectively, and onto the plane $P_{2,4}$, thereby providing vectors $v_{1,8}$ and $v_{4,4}$, respectively. The angles $\beta_3$ and $\beta_4$ between each pair of vectors may be computed and compared with the angular range of the second predetermined constraint.

In one exemplary method explained with reference to FIGS. 3A-3D and 4A-4D, the movement to be reproduced by the user (20) is defined by a first predetermined constraint for the orientations $v_1$ and $v_2$ of the user (20), and further defined by a second predetermined constraint for the orientations $v_1$ and $v_4$ of the user (20). In this exemplary method, the first predetermined constraint is considered to be the same of the example described in relation to FIGS. 3A-3D. Further, the second predetermined constraint is defined by an angular range (e.g. $AR_1$, for instance from 30° to 90°) and a plane definition (e.g. $P_2$) with which planes $P_{2,1}$, $P_{2,2}$, $P_{2,3}$ and $P_{2,4}$ are provided. The angle $\beta_1$ (corresponding to $t_1$) is comprised in $AR_1$ (i.e. $AR_{1,LOW} \leq \beta_1 \leq AR_{1,HIGH}$, where $AR_{1,LOW}$ and $AR_{1,HIGH}$ are the lower and upper limits of the angular range), therefore the user (20) is complying with the second predetermined constraint while reproducing the movement. The angle $\beta_2$ (corresponding to $t_2$) is comprised in $AR_1$, therefore the user (20) is complying with the second predetermined constraint while reproducing the movement. The angle $\beta_3$ (corresponding to $t_3$) is comprised in $AR_1$, therefore the user (20) is complying with the second predetermined constraint while reproducing the movement. The angle $\beta_4$ (corresponding to $t_4$) is not comprised in $AR_1$ (i.e. $\beta_4 \leq AR_{1,LOW}$ or $\beta_4 \geq AR_{1,HIGH}$), therefore the user (20) is not complying with the second predetermined constraint while reproducing the movement.

In this example, if only the orientations corresponding to time instants $t_1$ and $t_2$ were provided by motion tracking means, the method would determine that the user (20) correctly reproduced the movement since the first and second predetermined constraints are fulfilled (each of $\alpha_1$, $\alpha_2$, $\beta_1$ and $\beta_2$ complies with the conditions of the corresponding predetermined constraint). If the motion tracking means also provided the orientations of the user (20) corresponding to time instant $t_3$, since the angle $\beta_3$ is within $AR_1$ (and $SA_1 < \alpha_3 < EA_1$), the method would also determine that the user (20) correctly reproduced the movement. In contrast, if the motion tracking means also provided the orientations of the user (20) corresponding to time instant $t_4$, since the angle $\beta_4$ is outside $AR_1$ (and even though $SA_1 < \alpha_4 < EA_1$), the method would determine that the user (20) did not correctly reproduced the movement.

Figure 5:
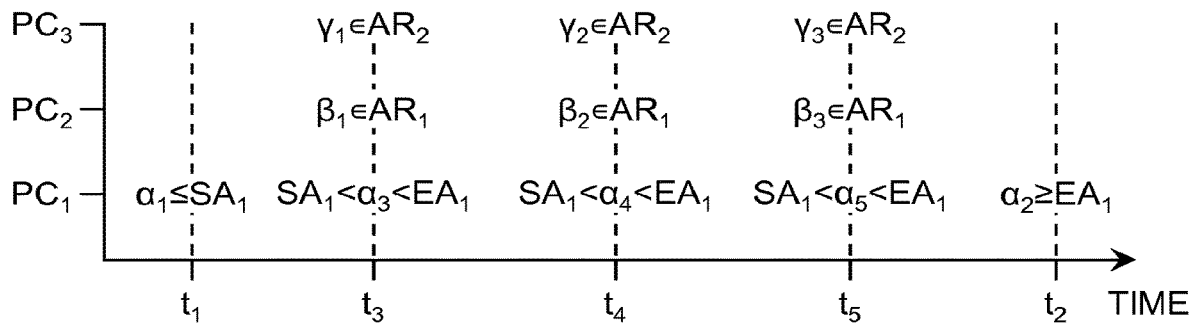
FIGS. 5-7 illustrate determination of correct reproduction of a movement with methods according to embodiments of the invention.

FIG. 5 illustrates determination of correct reproduction of a movement with a method according to an embodiment of the invention.

The movement is defined by three predetermined constraints (i.e. $PC_1$, $PC_2$, $PC_3$), each defined for a pair of orientations, and defined by a set of angles ($SA_1$, $EA_1$, $AR_1$, $AR_2$) and a plane definition. Motion tracking means provide orientations of a target in different time instants at least including time instants $t_1$ to $t_5$, each in a same global reference frame. Illustrated in the graph are the conditions that the computed angles ($\alpha$, $\beta$, $\gamma$) must fulfill for each of $PC_1$ to $PC_3$, for the different time instants, in order for the exemplary method to determine that the movement is correctly reproduced by the target.

In this embodiment, if for example at one time instant taking place before $t_2$ and after $t_1$ one of the conditions of any predetermined constraint is not fulfilled, the method determines that the movement is not correctly reproduced and the method is restarted so as to evaluate a subsequent movement of the target. For example, if one of the conditions corresponding to $t_4$ of $PC_1$-$PC_3$ is not fulfilled, the method does not further check whether the conditions corresponding to $t_5$ and $t_2$ of the predetermined constraints are fulfilled or not, but rather determines that the movement is not correctly reproduced and checks at a next time instant whether the condition of $t_1$ is fulfilled or not for the subsequent movement to be reproduced by the target.

In some examples, it may be determined that the target that was reproducing the movement did not carry out the entire motion of the movement as defined by the first predetermined constraint. Using for instance the example of FIG. 5, the computed angle(s) corresponding to the first predetermined constraint and to one or more consecutive time instants that are posterior to the first time instant $t_1$ may be compared with the computed angle(s) corresponding to previous time instants so as to determine if the target stopped carrying out the movement halfway. This is determined when the evolution of the computed angle gets closer to $SA_1$ than to $EA_1$ (as $SA_1$ is normally less than $EA_1$, then the evolution of the computed angle is decreasing) over time. Still referring to the example of FIG. 5, if the computed angle $\alpha_5$ is less than $\alpha_4$, and $\alpha_4$ is less than $\alpha_3$, and the difference of $\alpha_5$ and $\alpha_4$ (that is, the difference of the computed angles between two consecutive time instants), or the difference of $\alpha_5$ and $\alpha_3$ (that is, the entire difference of the computed angles corresponding to more than two consecutive time instants) is equal to or greater than a predefined decrease threshold, then it is determined that the reproduction of the movement is not correct and that, furthermore, the target stopped the movement halfway (for instance, if a person is the target, the person may have given up on the performance of the movement).

The first predetermined constraint may thus be also defined by the predefined decrease threshold, which is an angular difference that the computed angle(s) between two or more consecutive time instants must reach decreasingly. By way of example, if $SA_1$ is 30°, $EA_1$ is 90°, $\alpha_3$ is 51°, $\alpha_4$ is 45°, and $\alpha_5$ is 36°, if the predefined decrease threshold is 14°, then the method would determine that the target did not finish the movement at time instant $t_5$ because the reduction from $\alpha_3$ to $\alpha_5$ exceeds the predefined decrease threshold and because the computed angles $\alpha_4$, and $\alpha_5$ are less than previous consecutive computed angles (i.e. $\alpha_3 > \alpha_4 > \alpha_5$).

The feedback produced may reflect that the movement was not correctly reproduced because during reproduction of the same the target performed the movement in the direction reverse to that of the first predetermined constraint.

Figure 6:

FIG. 6 illustrates determination of correct reproduction of a movement with a method according to another embodiment of the invention.

The movement is defined by three predetermined constraints (i.e. $PC_1$, $PC_2$, $PC_3$), each defined for a pair of orientations, and defined by a set of angles ($SA_1$, $EA_1$, $AR_1$, $AR_2$) and a plane definition. Motion tracking means provide orientations of a target in different time instants at least including time instants $t_1$ and $t_2$, each orientation in a same global reference frame. Illustrated in the graph are the conditions that the computed angles must fulfill for each of $PC_1$ to $PC_3$, for the first and second time instants, in order for the exemplary method to determine that the movement is correctly reproduced by the target.

Figure 7:
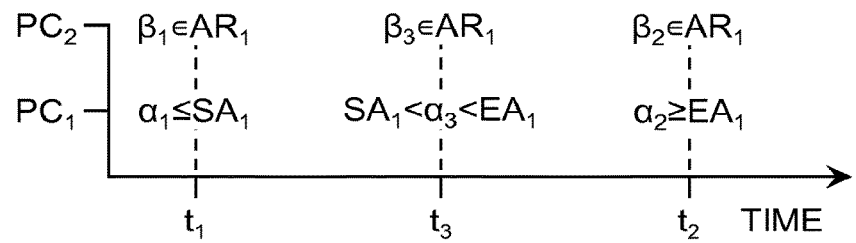

FIG. 7 illustrates determination of correct reproduction of a movement with a method according to another embodiment of the invention.

The movement is defined by two predetermined constraints (i.e. $PC_1$, $PC_2$), each defined for a pair of orientations, and defined by a set of angles ($SA_1$, $EA_1$, $AR_1$) and a plane definition. Motion tracking means provide orientations of a target in different time instants at least including time instants $t_1$, $t_2$ and $t_3$, each orientation in a same global reference frame. Illustrated in the graph are the conditions that the computed angles must fulfill for each of $PC_1$ and $PC_2$, for the first, second and third time instants, in order for the exemplary method to determine that the movement is correctly reproduced by the target.

Further, if in one exemplary embodiment (for instance as illustrated in FIG. 7) the first predetermined constraint is also defined by a predefined decrease threshold (e.g. 11°), if $SA_1$ is −20°, $EA_1$ is 45°, $\alpha_3$ is 39°, and $\alpha 2$ is 28° then the method would determine that the target did not finish the movement at time instant $t_2$. The reduction from $\alpha_3$ to $\alpha_2$ is equal to the predefined decrease threshold and the computed angle $\alpha_2$ is less than previous consecutive computed angles (i.e. $\alpha_3 > \alpha_2$).

FIGS. 8A-8B schematically illustrate a movement performed by the user (20).

The user (20) moves a right shoulder thereof upwards from a first position, illustrated in FIG. 8A, until it reaches a second position, illustrated in FIG. 8B. The movement of the shoulder does not involve an angular rotation of the limbs or joints (26-28) of the user (20), but rather a vertical displacement of the shoulder joint (28), which in turn involves the displacement of the arm and the remaining joints (26, 27) of said arm.

When the user (20) starts to perform the movement, the shoulder joint (28) accelerates ($a_1$) in a vertical direction. The user (20) ends the upwards movement of the shoulder upon stopping the vertical displacement of the joint (28), at which point the joint (28) is subject to an acceleration ($a_2$) in a direction opposite to the direction of the acceleration ($a_1$) for starting the movement. The accelerations ($a_1$, $a_2$) are measurable by, for instance, a sensor of motion tracking means attached to the shoulder or the upper arm; the sensor comprises an accelerometer providing the acceleration measurements including the directions of the measured accelerations.

FIG. 9 illustrates determination of correct reproduction of a movement with a method according to another embodiment of the invention.

The movement is defined by three predetermined constraints (i.e. $PC_1$, $PC_2$, $PC_3$): the first one ($PC_1$) defined for a first acceleration, and by a first direction and both start and end acceleration thresholds ($\kappa_1$, $\kappa_2$); the second one ($PC_2$) defined for a pair of orientations and by an angular range ($AR_1$) and a plane definition; and the third one ($PC_3$) defined for a second acceleration and by both a second direction and an acceleration interval ($AI_1$). Illustrated in the graph are the conditions that the measured accelerations and computed angle must fulfill for each of $PC_1$ to $PC_3$, for the first and second time instants, in order for the exemplary method to determine that the movement is correctly reproduced by the target.

Motion tracking means provide the first and second accelerations and the pair of orientations of a target in different time instants at least including time instants $t_1$ and $t_2$, each orientation in a same global reference frame. For example, two or more wearable sensors are arranged on an upper arm and a chest of a user such as the user (20) of FIGS. 8A-8B, and they provide orientation and acceleration measurements at the different time instants. As the first acceleration corresponds to the vertical movement of the shoulder, the first direction defined in the first predetermined constraint corresponds to a vertical direction, whereas the second direction defined in the third predetermined constraint may or may not coincide with the first direction, something which depends on the limitation applied to the movement to be performed. Regarding the latter, if for example the concerned acceleration limitation in the movement is in a direction ranging from −20° to 20° relative to a vertical plane, the second direction represents said range of directions.

The movement to be performed by the user, according to the three predetermined constraints, is a movement of the shoulder upwards while maintaining the chest relatively steady (accelerations being reduced in a direction parallel to a vertical axis and in directions forming an angle with the vertical axis up to 20° so that the shoulder is not moved due to a movement of the chest) and the upper arm not rotating (or not rotating substantially) relative to the chest. In this sense: the first acceleration measurements ($a_1$, $a_2$) correspond to the acceleration that the upper arm has been subjected to at the first and second time instants $t_2$, respectively, in the first direction; the computed angles ($\beta_1$, $\beta_2$) correspond to the relative angular differences between the orientations of the upper arm and the chest (and, thus, indicative of the relative angular movement between the two body members) at the first and second time instants ($t_1$, $t_2$), respectively; and the second acceleration measurements ($b_1$, $b_2$) correspond to the acceleration that the chest has been subjected to at the first and second time instants ($t_1$, $t_2$), respectively, in the second direction(s).

When the user starts the movement, the first acceleration ($a_1$) at $t_1$ must be greater than or equal to a start acceleration threshold (Ki, i.e. kappa subindex 1); for this, a device digitally processes the first acceleration so as to establish whether the measured acceleration is in the first direction or comprises a component in the first direction. Also, when the user starts the movement, the computed angle at $t_1$ shall be within the angular range ($AR_1$). When the user ends the movement, the first acceleration ($a_2$) at $t_2$ must be less than or equal to an end acceleration threshold ($\kappa_2$, i.e. kappa subindex 2); for this, the device digitally processes the second acceleration so as to establish whether the measured acceleration is in the second direction or comprises a component in the second direction. Also, when the user ends the movement, the computed angle at $t_2$ shall be within the angular range ($AR_1$). Additionally, as explained in more detail with reference to FIG. 10, at least one of the first and second time instants ($t_1$, $t_2$), but preferably at both time instants ($t_1$, $t_2$), the second acceleration ($b_1$, $b_2$) at the respective time instant shall be within the acceleration interval ($AI_1$) for determining that the movement has been correctly reproduced (when the first and second predetermined constraints are met). The acceleration interval ($AI_1$) is defined by upper and lower acceleration thresholds, said thresholds preferably being also part of the interval, therefore the second acceleration measurements may be equal to one of the thresholds in order to be within the interval.

FIG. 10 illustrates determination of correct reproduction of a movement with a method according to another embodiment of the invention, in line with the predetermined constraints of FIG. 9.

In the figure a chart is represented with a plurality of discrete values over time. A set of first acceleration 'a' values is represented with squares, a set of second acceleration 'b' values is represented with circles, and a set of computed angle 'β' values is represented with triangles. In the chart are also represented the start and end acceleration thresholds $\kappa_1$ and $\kappa_2$ (represented with dashed lines), upper and lower angle thresholds $A_1$ and $A_2$ (represented with dash-dotted lines) defining the angular range $AR_1$, and upper and lower acceleration thresholds $B_1$ and $B_2$ (represented with dotted lines) defining the acceleration interval $AI_1$.

In some embodiments, the magnitude of the acceleration 'a' and 'b' values corresponds to the norm of the acceleration measurements, yet the sign thereof is maintained based on the direction of the acceleration measurements. In some other embodiments, the magnitude of the acceleration 'a' and 'b' values corresponds to the acceleration component in the direction of the expected movement, that is to say, it corresponds to the part of the acceleration measurements that is parallel to the expected movement (in accordance with the direction defined in the respective predetermined constraint); the device carrying out the determination of correct reproduction of the movement processes the acceleration measurements so as to compute said acceleration component.

When the user starts to perform the shoulder movement, the first acceleration 'a' values start to raise in the first direction and are positive. At a first time instant 81, the acceleration 'a' value is above the start acceleration threshold ($\kappa_1$), thus the device carrying out the determination may consider that the user started the movement in accordance with the first predetermined constraint. Based on said predetermined constraint, the user is to end the movement when the acceleration 'a' value is below the end acceleration threshold ($\kappa_2$), something which occurs at a second time instant 84; prior to reaching that value, the acceleration 'a' further increased (after the first time instant 81) and then decreased.

During the time interval between the first and second time instants 81, 84, the computed angles 'β' were within the angular range ($AR_1$), thereby fulfilling the second predetermined constraint.

During that same time interval, the second acceleration 'b' values in the second direction were within the acceleration interval ($AI_1$) except for two values occurring at two intermediate time instants 82, 83. In some embodiments, second and/or further predetermined constraints (e.g. $PC_2$, $PC_3$, $PC_4$, etc.) defined for acceleration measurements are also defined by both a percentage threshold and a window size. In these embodiments, the device digitally evaluating the fulfillment of the predetermined constraints provides a sliding window with a size in number of samples equal to the window size, and every time it receives a new acceleration value corresponding to that/those predetermined constraint(s), the window slides so as to encompass the most recent acceleration value while removing the oldest acceleration value inside the window if the window was full (i.e. had as many samples as the window size). The device considers that the predetermined constraint(s) is/are fulfilled if every time the sliding window is filled with samples at least a number N of samples inside the window is within the acceleration interval $AI_1$, and the ratio N over the window size is equal to or greater than the percentage threshold. Accordingly, if the window size is 10, and the percentage threshold is 70%, at least 7 samples inside the window (while the window is filled with 10 samples) are within $AI_1$. In some other embodiments, second and/or further predetermined constraints do not have the percentage threshold and the window size defined, thus for fulfilling the corresponding predetermined constraints all the acceleration samples occurring during the movement (in this example, between the first and second time instants 81, 84) need be within the acceleration interval ($AI_1$).

In the present example of FIG. 10, the third predetermined constraint ($PC_3$) is defined by a percentage threshold of 60% and a window size of 5, hence even if two second acceleration 'b' values at two intermediate time instants 82, 83 fall outside the acceleration interval ($AI_1$), the predetermined constraint is met because the sliding window every time has at least three of the five acceleration 'b' values thereof within the acceleration interval ($AI_1$) between the first and second time instants 81, 84. In this case, the sliding window becomes full of samples at the time instant posterior to the second intermediate time instant 83, therefore the sliding window will slide three times, and the third predetermined constraint ($PC_3$) will be processed four times between the first and second time instants 81, 84.

As all three predetermined constraints are fulfilled, the device determines that the user correctly reproduced the movement.

Figure 11:
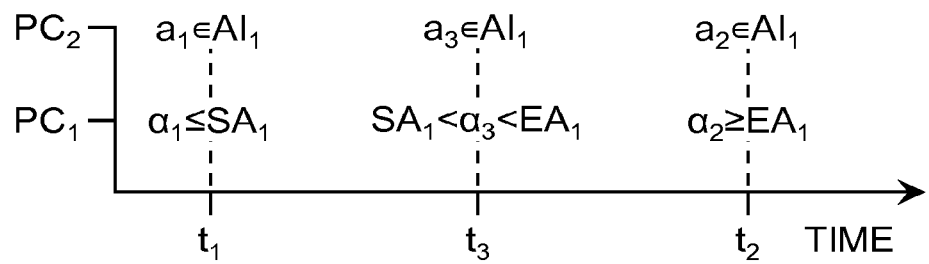

FIG. 11 illustrates determination of correct reproduction of a movement with a method according to another embodiment of the invention.

The movement is defined by two predetermined constraints (i.e. $PC_1$, $PC_2$): the first one ($PC_1$) for a pair of orientations, and defined by a set of angles ($SA_1$, $EA_1$, $AR_1$) and a plane definition, and the second one ($PC_2$) defined for an acceleration and by both a first direction and an acceleration interval ($AI_1$). Illustrated in the graph are the conditions that the computed angles and the acceleration measurements must fulfill for each of $PC_1$ and $PC_2$, for first, second and third time instants in order for the exemplary method to determine that the movement is correctly reproduced by the target. In some examples, the second predetermined constraint ($PC_2$) is also defined by a percentage threshold and a window size, in which cases it may occur that the acceleration measurements do not have to fall within the acceleration interval ($AI_1$) in all three time instants ($t_1$, $t_2$, $t_3$).

Motion tracking means provide the acceleration and the pair of orientations of a target in different time instants at least including time instants $t_1$, $t_2$, $t_3$, each orientation in a same global reference frame. The values of the acceleration measurements (i.e. $a_1$, $a_2$, $a_3$) may be the norm of the acceleration measurements maintaining the sign thereof based on both the direction of the acceleration measurements and the first direction, or the acceleration component in the direction of the expected movement (i.e. the first direction) to be performed by the target.

Figure 12:
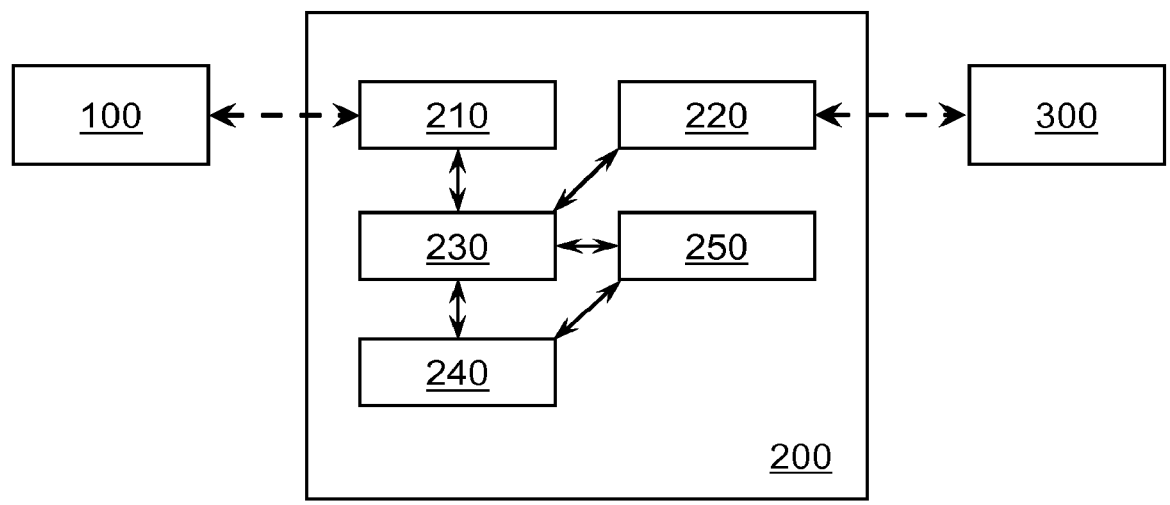
FIG. 12 schematically illustrates the main elements of a device and a system of the invention, according to an embodiment thereof.

FIG. 12 schematically shows a system according to an embodiment of the invention. The system comprises a motion tracking means (100), a device (200) according to an embodiment of the invention, and a remote server (300). Motion tracking means (100) may be implemented with any technology known in the state of the art, capable of providing orientation and/or acceleration information, individualized for one, two or more body segments (that is, limbs, parts of limbs, or any other part of the body with articulation capabilities). Some non-limiting examples of known technologies for these motion tracking means (100) are 3D image capture techniques, wearable transmission devices connected to external triangulation receptors, wearable sensors including, for example, gyroscopes, magnetometers, and/or accelerometers (e.g. wearable accelerometers). Regardless of the particular implemented technology, at least a first orientation ($v_1$) and a second orientation ($v_2$) of at least two segments of the user's body are provided to the device (200), and/or at least a first acceleration ($a_1$) of at least a segment of the user's body is provided to the device (200).

The motion tracking means (100) provide the orientations and/or accelerations together with an identification of each orientation and/or acceleration, for example an identification of the sensor providing the orientation and/or acceleration, or an identification of the segment or limb associated with the orientation and/or acceleration. The device (200) uses the identification of the orientations and/or accelerations to select the particular orientations and/or accelerations for which each predetermined constraint is defined; similarly, in a method for determining a correct reproduction of a movement according to the present disclosure, the particular orientations and/or accelerations for which each predetermined constraint is defined are selected so as to carry out the different steps of the method.

The device (200) comprises first communication means (210) for receiving the orientation and/or acceleration information from the motion tracking means (100), that is, the first orientation ($v_1$), the second orientation ($v_2$), and any additional orientation vectors, and/or, the first and/or further accelerations, of the different time instants, required for determining the correct execution of the particular movement under analysis. The first communication means (210) may be implemented according to a technology and protocol known in the state of the art, and may either be a direct connection or include any number of intermediate connection networks.

The device (200) comprises second communication means (220) through which it may transmit and/or receive data to the remote server (300) (e.g. a user may transmit data regarding the definition of movements and/or predetermined constraints, such as updated ranges of constraints, a user may also transmit data for selecting a movement to be assessed so that the appropriate angular ranges and/or acceleration intervals for validating the movement are selected, etc.). Said second communication means (220) may be implemented according to a technology and protocol known in the state of the art, and may be a direct connection or include any number of intermediate connection networks. In a non-limiting example, said remote server (300) may be a database from which a user may then retrieve information about the movements being tracked, for instance through a personal device such as a computer or a phone.

The first communication means (210) and the second communication means (220) may be implemented either with the same technology, sharing the same physical resources, or with different technologies known in the state of the art. Some embodiments of the invention may be implemented without the remote server (300). In this case, feedback regarding whether the movement is correctly reproduced, as determined by the device (200), may be stored in an internal memory (240) of the device (200) or displayed for the user's knowledge through any kind of user interface (250) of the device (200). Through the user interface (250), a user may also select the angular ranges and/or acceleration intervals of each constraint, and select which movement or movements are to be analyzed.

Once the first orientation ($v_1$) and the second orientation ($v_2$) are received by the device (200), the predetermined constraints of the movement under analysis are verified at the processor (230). For said verification, the device (200) is configured to access the memory (240) for gathering which orientations and, thus, body segments need to be compared (i.e. the vectors provided by the motion tracking means 100 associated with said body segments), the plane(s) onto which said vectors are to be projected, and the angular conditions that need to be met. Additionally or alternatively, once the first acceleration is received by the device (200), the predetermined constraints of the movement under analysis are verified at the processor (230). For said verification, the device (200) is configured to access the memory (240) for gathering which accelerations and, thus, body segments need to be compared (i.e. the acceleration measurements provided by the motion tracking means 100 associated with said body segments), the direction, and the start and end acceleration thresholds that need to be met.

Even though in the present disclosure it is explained that the start angle is less than the end angle so that the first computed angle (concerning the first predetermined constraint) must be less than or equal to the start angle and the second computed angle (concerning the first predetermined constraint) must be greater than or equal to the end angle in order to correctly reproduce the movement, it is readily apparent that it is also possible that the angles of the first predetermined constraint may be defined the other way around, that is, the start angle is greater than the end angle. In that case, the first computed angle must be greater than or equal to the start angle, and the second computed angle must be less than or equal to the end angle in order to determine that the movement has been reproduced correctly. Similarly, even it is explained that the first acceleration value must be greater than or equal to the start acceleration threshold and the second acceleration value must be less than or equal to the end acceleration threshold (concerning the first predetermined constraint) in order to determine that the movement is correctly reproduced, it is readily apparent that it is also possible to define these thresholds or the direction defined in the first predetermined constraint the other way around. In that case, the first acceleration value must be less than or equal to the start acceleration threshold, and the second acceleration value must be greater than or equal to the end acceleration threshold in order to determine that the movement has been reproduced correctly.

In this text, the term "time instant" is meant to refer to a particular moment of time, but it is readily apparent that it may involve a time duration, that is as short as possible, inherent to the speed and/or synchronization of the devices. For example, the motion tracking means may not provide the orientations of a target in a moment of time but in a short time duration. The time duration is preferably less than 100 milliseconds, and more preferably less than 50 ms, 25 ms, 10 ms and/or 5 ms.

In this text, the term "comprises" and its derivations (such as "comprising", etc.) should not be understood in an excluding sense, that is, these terms should not be interpreted as excluding the possibility that what is described and defined may include further elements, steps, etc.

Even though the terms first, second, third, etc. have been used herein to describe several parameters or variables, it will be understood that the parameters or variables should not be limited by these terms since the terms are only used to distinguish one parameter or variable from another. For example, the second time instant or $t_2$ could as well be named third time instant or $t_3$, and the third time instant or $t_3$ could be named second time instant or $t_2$ without departing from the scope of this disclosure.

On the other hand, the invention is obviously not limited to the specific embodiment(s) described herein, but also encompasses any variations that may be considered by any person skilled in the art (for example, as regards the choice of materials, dimensions, components, configuration, etc.), within the general scope of the invention as defined in the claims.

The invention claimed is:

1. A computer-implemented method for determining a reproduction of a movement of a user according to a predetermined movement constraint for an exercise, comprising:
    (a) receiving, from a motion tracking system, first and second orientations at a first time and third and fourth orientations at a second time;
    (b) projecting the first and second orientations at the first time onto a first plane;
    (c) projecting the third and fourth orientations at the second time onto a second plane;
    (d) computing a first calculation based on the first and second orientations projected onto the first plane and a second calculation based on the third and fourth orientations projected onto the second plane; and
    (e) determining the reproduction of the movement based at least in part on a comparison of the first calculation and the second calculation with the predetermined movement constraint.

2. The computer-implemented method of claim 1, wherein the first and second orientations are projected onto the first plane as a first pair of vectors.

3. The computer-implemented method of claim 2, wherein the third and fourth orientations are projected onto the second plane as a second pair of vectors.

4. The computer-implemented method of claim 3, wherein computing the first calculation comprises computing a first angle between the first pair of vectors and computing the second calculation comprises computing a second angle between the second pair of vectors.

5. The computer-implemented method of claim 1, wherein the predetermined movement constraint comprises a constraint on range of movement for the exercise.

6. The computer-implemented method of claim 5, wherein the constraint on range of movement comprises an angular range or a start angle and an end angle that limit the range of movement by the user for performing the exercise.

7. The computer-implemented method of claim 5, wherein the predetermined movement constraint further comprises a constraint on one or more accelerations corresponding to the movement of the user.

8. The computer-implemented method of claim 1, wherein the first plane and the second plane each corresponds to an orientation of the user and are defined according to the predetermined movement constraint.

9. The computer-implemented method of claim 8, wherein each the orientation of the user is an orientation of a limb or body segment.

10. The computer-implemented method of claim 9, wherein the limb or body segment comprises a leg, upper arm, lower arm or forearm, head, or torso.

11. The computer-implemented method of claim 1, wherein the exercise comprises a physical therapy exercise.

12. The computer-implemented method of claim 1, wherein the computer-implemented method is performed in real-time.

13. The computer-implemented method of claim 12, further wherein the reproduction of movement is determined to be correct or incorrect.

14. The computer-implemented method of claim 13, wherein the reproduction of movement is determined to be incorrect when the movement does not fulfill the predetermined movement constraint.

15. The computer-implemented method of claim 13, further comprising providing feedback to the user indicating the reproduction of movement is correct or incorrect.

16. The computer-implemented method of claim 15, wherein the feedback indicates what condition of the predetermined movement constraint has not been fulfilled.

17. The computer-implemented method of claim 1, wherein the user is a person or an object.

18. The computer-implemented method of claim 17, wherein the object is a robot, an exoskeleton, or an exosuit.

19. The computer-implemented method of claim 17, wherein the motion tracking system comprises a first sensor adapted to measure the first orientation at the first time and the third orientation at the second time and a second sensor adapted to measure the second orientation at the first time and the fourth orientation at the second time.

20. The computer-implemented method of claim 19, wherein the first sensor and the second sensor each comprise an accelerometer and a gyroscope.

* * * * *